(12) United States Patent
Ishihara et al.

(10) Patent No.: US 8,131,520 B2
(45) Date of Patent: *Mar. 6, 2012

(54) CANCER DIAGNOSTIC DEVICE

(75) Inventors: Hideki Ishihara, Miki (JP); Tomoko Matsushima, Kobe (JP)

(73) Assignee: Sysmex Corporation, Kobe, Hyogo (JP)

( * ) Notice: Subject to any disclaimer, the term of this patent is extended or adjusted under 35 U.S.C. 154(b) by 667 days.

This patent is subject to a terminal disclaimer.

(21) Appl. No.: 12/286,699

(22) Filed: Oct. 1, 2008

(65) Prior Publication Data

US 2009/0105960 A1    Apr. 23, 2009

(30) Foreign Application Priority Data

Oct. 2, 2007   (JP) ................................. 2007-259254

(51) Int. Cl.
*G06F 7/60* (2006.01)
*G06F 19/00* (2011.01)
*G06F 15/00* (2006.01)
*C12Q 1/25* (2006.01)

(52) U.S. Cl. ........................ 703/2; 702/19; 700/1; 435/4

(58) Field of Classification Search ........................ None
See application file for complete search history.

(56) References Cited

U.S. PATENT DOCUMENTS

| | | |
|---|---|---|
| 2002/0095259 A1 | 7/2002 | Hood et al. |
| 2003/0233197 A1 | 12/2003 | Padilla et al. |
| 2006/0017362 A1 | 1/2006 | Uno et al. |
| 2006/0173632 A1 | 8/2006 | Torikoshi et al. |
| 2007/0003438 A1 | 1/2007 | Kobayashi et al. |
| 2007/0077658 A1* | 4/2007 | Kobayashi et al. ............. 436/63 |
| 2007/0231837 A1 | 10/2007 | Ishihara et al. |

OTHER PUBLICATIONS

European Search Report dated Feb. 12, 2009 for European Patent Application No. 08165486.5.

Sgambato, A.; Camerini, A.; Pani, G.; Cangiano, R.; Faraglia, B.; Bianchino, G.; De Bari, B.; Galeotti, T.; Cittadini, A. "Increased Expression of Cyclin E is Associated with an Increased Resistance to Doxorubicin in Rat Fibroblasts," *British Journal of Cancer*, 2003, 88, pp. 1956-1962.

* cited by examiner

*Primary Examiner* — John S Brusca

(74) *Attorney, Agent, or Firm* — Brinks Hofer Gilson & Lione

(57) ABSTRACT

A device for supporting a diagnosis of a cancer which provides information useful to decide whether or not an anthracycline anticancer drug should be administered to a cancer patient to be examined is disclosed. Concretely, the device is composed to be able to acquire an activity and an expression of two cyclin dependent kinases (CDK) from a malignant tumor of a cancer patient to be examined, and to acquire a CDK parameters from both of two CDKs. Furthermore the device determines sample data comprising predetermined CDK parameter, and display information of determined sample data. According to the above component, user is easily able to know whether or not a cancer of a cancer patient, whose tumor is similar to the tumor of the cancer patient to be examined, has been recurred in spite of an administration of an anthracycline anticancer drug.

20 Claims, 27 Drawing Sheets

CANCER DIAGNOSTIC DEVICE

RELATED APPLICATIONS

This application claims priority under 35 U.S.C. §119 to Japanese Patent Application No. JP2007-259254 filed Oct. 2, 2007, the entire content of which is hereby incorporated by reference.

BACKGROUND OF THE INVENTION

Field of the Invention

The present invention relates to a device for supporting a diagnosis of a cancer and a device for predicting an effects of anthracycline anticancer drugs.

Chemotherapy, that is, treatment by anticancer drugs is being conventionally carried out at one of the treatment methods on cancer patients. The treatment by anticancer drugs is an extremely useful treatment method to suppress the progress of cancer and to suppress recurrence of cancer, but also involves risks of side effects.

With anticancer drugs, it is known that its effectiveness differs by individual patients, and although some patients take the risk of side effects, great number of patients who cannot sufficiently obtain the anticancer effect from the anticancer drugs exist. In order to solve such problem, various proposals have been made for predicting the effectiveness (sensitivity) of the anticancer drugs in a cancer patient and providing a maximum anticancer drug treatment while avoiding the risk of unnecessary side effects.

In US 2006/0173632, US 2007/0003438, or US 2007/0231837, a method of determining sensitivity of the taxane anticancer drugs based on the activity value and the expression level of the cyclin-dependent kinase (CDK) is disclosed.

It is also known that anticancer drugs have different effects on the living body depending on the type. For instance, the taxane anticancer drug stops the mitotic division of cells by stabilizing the microtubules in the cell in a polymerized state, and induces apoptosis. The main side effects of the taxane anticancer drug are known as peripheral neuritis. The drugs having the effect of inhibiting the topoisomerase include anthracycline anticancer drugs. The anthracycline anticancer drugs is an anticancer drug having a strong aggressiveness to directly break the DNA, and involves major side effects such as breaking of myocardial cell membrane and congestive failure. Thus, it is particularly important to predict the sensitivity of the anthracycline anticancer drugs in the cancer treatment using the anthracycline anticancer drugs.

BRIEF SUMMARY

A first aspect of the invention is a device for supporting a diagnosis of a cancer comprising: acquiring means for acquiring a first cyclin dependent kinase (first CDK) parameter which is capable to be acquired from an activity value and an expression level of the first CDK, and a second cyclin dependent kinase (second CDK) parameter which is capable to be acquired from an activity value and an expression level of the second CDK, based on an activity value and an expression level of the first CDK contained in a first malignant tumor of a cancer patient to be examined and on an activity value and an expression level of the second CDK contained in the first malignant tumor; a memory storing a plurality of sample data, each of the sample data comprising: a first CDK parameter acquired from an activity value and an expression level of the first CDK contained in a second malignant tumor of a sample patient, to whom anthracycline anticancer drugs have been administered; a second CDK parameter acquired from an activity value and an expression level of the second CDK contained in the second malignant tumor; and information regarding a cancer recurrence of the sample patient; selecting means for selecting one of the sample data stored in the memory whose first CDK parameter and second CDK parameter are in a prescribed range, wherein the range contains the first CDK parameter and the second CDK parameter of the cancer patient to be examined; and display means for displaying the information regarding a cancer recurrence comprised in the selected sample data.

A second aspect of the invention is A device for supporting a diagnosis of a cancer comprising: display; and controller, including a memory under control of a processor, the memory storing a plurality of sample data, each of the sample data comprising: first cyclin dependent kinase (first CDK) parameter which is capable to be acquired from an activity value and an expression level of the first CDK contained in a first malignant tumor of a sample patient who has been administered anthracycline anticancer drugs; second cyclin dependent kinase (second CDK) parameter which is capable to be acquired from an activity value and an expression level of the second CDK contained in the second malignant tumor; and information regarding a cancer recurrence of the sample patient, and instructions enabling the processor to carry out operations, comprising: acquiring a first CDK parameter based on an activity value and an expression level of the first CDK contained in a second malignant tumor of a cancer patient to be examined, and a second CDK parameter based on an activity value and an expression level of the second CDK contained in the second malignant tumor; selecting one of the sample data stored in the memory whose first CDK parameter and second CDK parameter are in a prescribed range, wherein the range contains the first CDK parameter and the second CDK parameter of the cancer patient to be examined; and controlling the display to display the information regarding a recurrence comprised in the selected sample data.

A third aspect of the invention is a device for predicting an effects of anthracycline anticancer drugs comprising: acquiring means for acquiring a first cyclin dependent kinase (first CDK) parameter which is capable to be acquired from an activity value and an expression level of the first CDK, and a second cyclin dependent kinase (second CDK) parameter which is capable to be acquired from an activity value and an expression level of the second CDK, based on an activity value and an expression level of the first CDK contained in a first malignant tumor of a cancer patient to be examined and on an activity value and an expression level of the second CDK contained in the first malignant tumor; a memory storing a plurality of sample data, each of the sample data comprising: a first CDK parameter acquired from an activity value and an expression level of the first CDK contained in a second malignant tumor of a sample patient, who has been administered anthracycline anticancer drugs; a second CDK parameter acquired from an activity value and an expression level of the second CDK contained in the second malignant tumor; and information regarding a cancer recurrence of the sample patient; selecting means for selecting one of the sample data stored in the memory whose first CDK parameter and second CDK parameter are in a prescribed range, wherein the range contains the first CDK parameter and the second CDK parameter of the cancer patient to be examined; predicting means for predicting an effects of anthracycline anticancer drugs with the cancer patient to be examined based on the information of the selected sample data; and displaying means for displaying the result of the prediction.

A fourth aspect of the invention is a device for predicting an effects of anthracycline anticancer drugs comprising: acquiring means for acquiring a first cyclin dependent kinase (first CDK) parameter which is capable to be acquired from an activity value and an expression level of the first CDK, and a second cyclin dependent kinase (second CDK) parameter which is capable to be acquired from an activity value and an expression level of the second CDK, based on an activity value and an expression level of the first CDK contained in a first malignant tumor of a cancer patient to be examined and on an activity value and an expression level of the second CDK contained in the first malignant tumor; a memory storing a standard value capable to divide a group of cancer patients into unless two groups different in a risk of cancer recurrence based on a first CDK parameter and a second CDK parameter, wherein the patients have not been administered anthracycline anticancer drugs; comparing means for comparing the first CDK parameter and the second CDK parameter of the cancer patient to be examined with the standard value stored in the memory; predicting means for predicting an effects of anthracycline anticancer drugs with the cancer patient to be examined based on the result of the comparing; and displaying means for displaying the result of prediction.

DETAILED DESCRIPTION OF THE PREFERRED EMBODIMENTS

A device for supporting a diagnosis of a cancer of the present invention, a device for predicting effectiveness of the anthracycline anticancer drugs of the present invention, and a method of predicting the effectiveness of the anthracycline anticancer drugs in a cancer patient to be examined of the present invention will be described in detail below with reference to the accompanying drawings.

Malignant tumors are tumors that invade or metastasize to other tissues, and enlarge at various sites of the body thereby threatening the life. The malignant tumor includes cancer or malignant tumor originating from epithelial tissue, and sarcoma or malignant tumor originating from non-epithelial tissue. Specifically, the malignant tumor includes malignant tumors forming at positions such as breast, lung, liver, stomach, large intestine, pancreas, uterus, testis, ovaria, thyroid, accessory thyroid, lymphography, and the like. The malignant tumor can be obtained from cancer patients having breast cancer, lung cancer, liver cancer, gastric cancer, large intestine cancer, pancreas cancer, prostate cancer, and the like.

[1] CDK Serving as Parameter in Cancer

The cyclin-dependent kinase (CDK) accurately reflects and represents the state of malignant tumor in a patient with cancer. The CDK shows similar profile for cancer patients having malignant tumors of a similar state. Thus, the likeliness of the cancer to recur, the effectiveness of the anticancer drug, and the like can be evaluated based on a first parameter acquired from an activity value and an expression level of a first CDK in the malignant tumor and a second parameter acquired from an activity value and an expression level of a second CDK in the malignant tumor.

The recurrence refers to a case where the same malignant tumor reappears in the remaining organs after an organ is partially removed to extirpate the malignant tumor, and a case where the tumor cell is separated from a primary tumor and conveyed to a remote tissue (remote organ), and independently grows thereat (metastasize and recur). Generally, "likely to recur" refers to a case where there is a possibility the cancer will recur within five years after the extirpative surgery. Since the death rate of the patients recognized with recurrence within five years is high, predicting the recurrence within five years after the extirpative surgery has clinical meaning. In stage classification, stage III has a recurrence rate of 50%, and recurrence is likely to occur compared to stage II (recurrence rate of 20%).

In the present specification, the cyclin-dependent kinase is a collective term of a phosphorylated enzyme group activated by being bounded to cyclin. The cyclin-dependent kinase functions in a specific time of the cell cycle depending on the type thereof. In the present specification, the CDK inhibitor is a collective term of a factor group that bonds with the cyclin CDK complex and inhibits the activity of the cyclin CDK complex.

Figure 14:
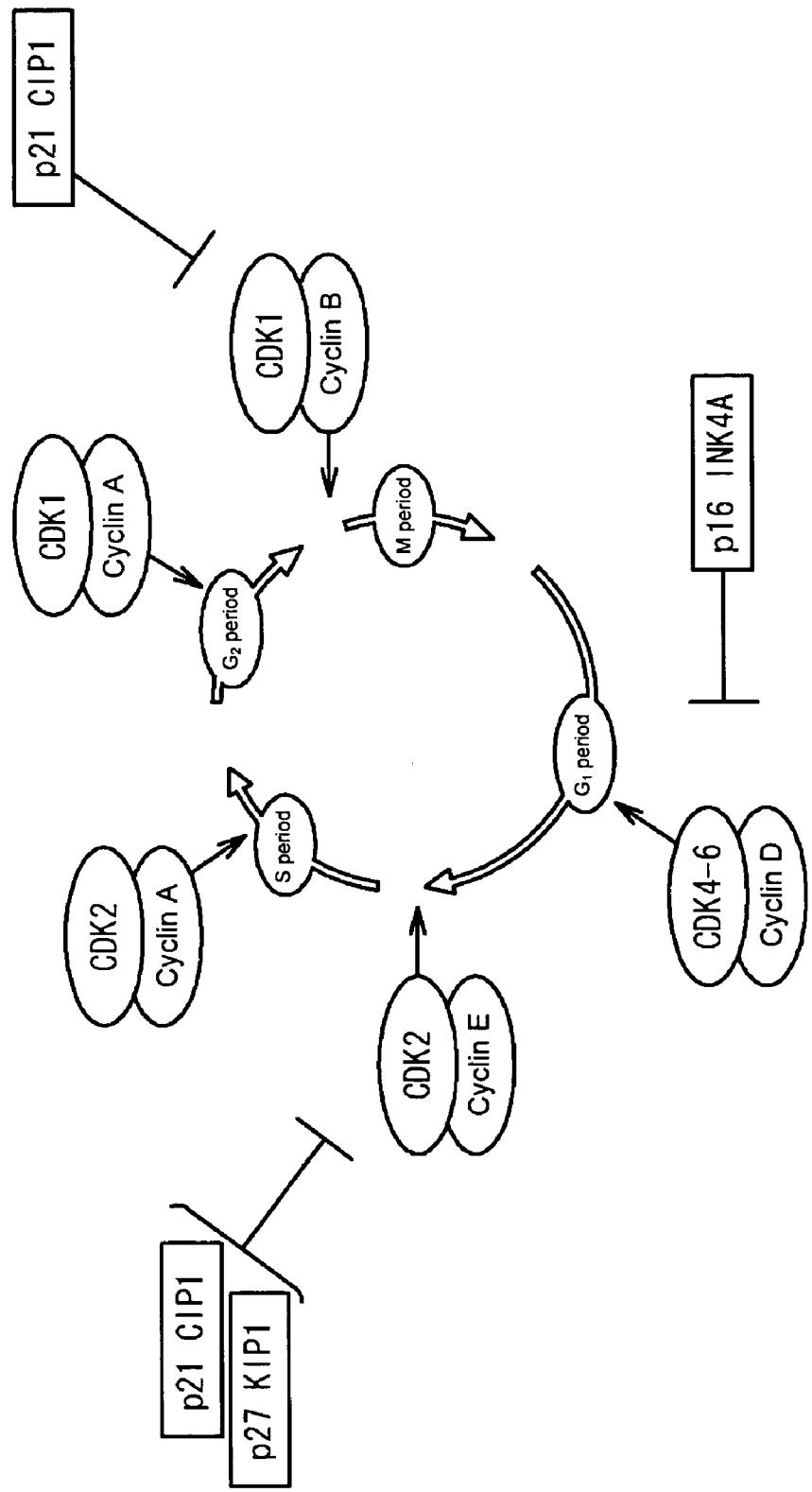
FIG. 14 is a view schematically describing a cell cycle.

The cell cycle is a cycle that the cell starts to grow and return to the starting point as two daughter cells after events of DNA replication, distribution of chromosomes, nuclear division, cytoplasmic division, and the like. The cell cycle is divided into four periods of $G_1$ period, S period, $G_2$ period, and M period, as shown in FIG. 14. The S period is the replication period of DNA, and the M period is the division period. The $G_1$ period is a preparation period for the cell to enter the S period between the completion of mitotic division and the start of DNA synthesis. After passing a critical point (point R in animal cell) in the $G_1$ period, the cell cycle starts, and normally completes one cycle without stopping in the middle. The $G_2$ period is a preparation period for the cell to enter the M period between the termination of DNA synthesis and the start of mitotic division. Main check points of the cell cycle is immediately before entering the S period from the $G_1$ period ($G_1$ check point), and the transition period ($G_2$/M check point) from the $G_2$ period to mitotic division. In particular, the $G_1$ check point is important as it triggers the start of the S period. This is because, after passing a certain point of the $G_1$ period, the cell advances the cell cycle as S period □ $G_2$ period □ M period □ $G_1$ period without stopping the growth even if a growth signal is not provided. The cell that has stopped growing enters a rest period ($G_0$) having DNA content of the $G_1$ period, and the state deviates from the cell cycle. Due to growth induction, the cell can advance to the S period after a time slightly longer than the $G_1$ period in the cell cycle.

The CDK is not particularly limited, and may be CDK1, CDK2, CDK4, CDK6, and the like. The CDK also includes CDK belonging to cyclin A-dependent kinase, CDK belonging to cyclin B-dependent kinase, CDK belonging to cyclin D-dependent kinase, CDK belonging to cyclin E-dependent kinase, and the like. The cyclin A-dependent kinase is not particularly limited as long as it is CDK that indicates activity by being bound to cyclin A, but includes CDK1, CDK2, and the like. The cyclin B-dependent kinase is not particularly limited as long as it is CDK that indicates activity by being bound to cyclin B, but includes CDK1 and the like. The cyclin D-dependent kinase is not particularly limited as long as it is CDK that indicates activity by being bound to cyclin D, but includes CDK4, CDK6, and the like. The cyclin E-dependent kinase is not particularly limited as long as it is CDK that indicates activity by being bound to cyclin E, but includes CDK2 and the like.

Such CDK activates a predetermined period of the cell cycle as shown in table 1 by being a cyclin-CDK complex (hereinafter also referred to as "active CDK") bound to the corresponding cyclin, as shown in table 1. For instance, CDK1 becomes active by binding to cyclin A or B, CDK2 becomes active by binding to cyclin A or E, and CDK4 and CDK6 become active by binding to cyclin D1, cyclin D2, or cyclin D3. The CDK activity sometimes has the activity inhibited by the CDK inhibitor as shown in table 1. For instance, p21 inhibits CDK1 and CDK2, p27 inhibits CDK2, CDK4, and CDK6, and p16 inhibits CDK4 and CDK6.

TABLE 1

| CDK | Binding cyclin | Binding CDK inhibitor | Operating period of active CDK |
|---|---|---|---|
| CDK4 | Cyclin D1 | p27, p16 | $G_1$ period |
| CDK6 | Cyclin D2 Cyclin D3 | | |
| CDK2 | Cyclin E | p27 | $G_1$ period → S period transition |
| CDK2 | Cyclin A | p21, p27 | S period active |
| CDK1 | Cyclin A Cyclin B | p21 | $G_2$ period → M period transition |
| Cyclin A-dependent kinase | Cyclin A | p21, p27 | CDK1: $G_2$ period → M period CDK2: middle period of S period |
| Cyclin B-dependent kinase | Cyclin B | p21 | CDK1: $G_2$ period → M period |
| Cyclin D-dependent kinase | Cyclin D | p27, p16 | CDK4, CDK6: $G_1$ period |

Among the CDKs, the activity value and the expression level of the first CDK are measured and the first parameter is acquired from the activity value and the expression level, and the activity value and the expression level of the second CDK are measured and the second parameter is acquired from the activity value and the expression level. The first parameter is a ratio of the expression level and the activity value of the first CDK, specifically, the specific activity represented with the following equation (I):

$$\text{Specific activity of first CDK} = \text{activity value of first CDK/expression level of first CDK} \quad (I)$$

The second parameter is a ratio of the expression level and the activity value of the second CDK, specifically, the CDK specific activity represented with the following equation (II):

$$\text{Specific activity of second CDK} = \text{activity value of second CDK/expression level of second CDK} \quad (II)$$

The CDK activity value refers to the level (unit is expressed as U (unit)) of the kinase activity calculated from the amount of substrate that binds with a specific cyclin, and phosphorylates the cyclin. The substrate to which the CDK phosphorylates includes histon H1 for active CDK1 and active CDK2, and Rb (retinoblastoma protein) for active CDK4 and active CDK6. The CDK activity value can be measured with a conventional CDK activity measurement method. Specifically, there may be a method of preparing a specimen containing the active CDK from the cell dissolved solution of the measurement specimen, retrieving $^{32}P$ into the substrate protein by using the relevant specimen and the $^{32}P$ labeled ATP ($\gamma$-[$^{32}P$]-ATP), measuring the labeled quantity of the $^{32}P$ labeled phosphorylated substrate, and determining the quantity based on the standard curve created with a standard product. A method that does not use label of the radioactive substance includes a method disclosed in Japanese Laid-Open Patent Publication No. 2002-335997. This method is a method of preparing a specimen containing the target active CDK from the cell solubilizing solution of the measurement specimen, reacting adenosine 5'-O-(3-thiotriphosphate) (ATP-$\gamma$S) and the substrate protein, introducing monothiophosphate group to serine residue or threonine residue of the substrate protein, bonding fluorescent labeled substance or labeled enzyme to the sulfur atom of the introduced monothiophosphate group to label the substrate protein, measuring the labeled quantity (fluorescence quantity when fluorescent labeled substance is used) based on the labeled thiophosphate group, and determining the quantity based on the standard curve created with the standard product.

The specimen provided for activity measurement is prepared by specifically obtaining the target CDK from the solubilizing solution of the tissue containing the malignant tumor to be measured. In this case, the specimen may be prepared using an anti-CDK antibody specific to the target CDK. The specimen may be prepared using an anti-cyclin antibody in the case of activity measurement of a specific cyclin-dependent kinase (e.g., cyclin A-dependent kinase, cyclin B-dependent kinase, cyclin E-dependent kinase). In either case, the specimen contains CDK other than the active CDK. For instance, the specimen contains a complex in which the CKD inhibitor is bound to the cyclin CDK complex. When the anti-CDK antibody is used, the specimen contains CDK single body, complex of CDK and cyclin and/or CDK inhibitor, complex of CDK and other compound, and the like. Therefore, the activity value is measured as a unit (U) calculated from the amount of phosphorylated substrate under a state that active type, inactive type, and various competitive reactions coexist.

The CDK expression level is the target CDK level (unit corresponding to number of molecules) measured from the cell solubilizing solution, and is measured with a conventionally known method of measuring the target protein quantity from the protein mixture. For instance, ELISA method, western blot method, and the like may be used, or measurement may be carried out with a method disclosed in Japanese Laid-Open Patent Publication No. 2003-130871. The target protein (CDK) is captured using a specific antibody. For instance, all the CDK1 existing within the cell (including CDK single body, complex of CDK and cyclin and/or CDK inhibitor, complex of CDK and other compound) can be captured using the anti-CDK1 antibody.

Therefore, the specific activity calculated from the equations (I) and (II) corresponds to the proportion of the CDK indicating activity of the CDK existing in the cell, and is the CDK activity level based on the growth state of the malignant tumor cell, which is the target of determination. The CDK specific activity thus obtained does not depend on the measurement specimen preparation method. In particular, the measurement specimen (cell solubilizing solution) prepared from the biopsy material is likely to be influenced by the size of non-cellular tissues such as extracellular matrix contained in the actually collected tissue. Therefore, there is a large meaning to use the specific activity in which such influence is eliminated, and the correlation with the clinical characteristics is high compared to the simple activity value.

Which CDK activity is superior can be known from the specific activity of the first CDK and the specific activity of the second CDK, whereby the extent of the cell proportion in any period of the cell cycle can be known, or the cell proportion of which period is superior can be known.

The type of CDK for measuring the specific activity is not particularly limited, and may be appropriately selected. Generally, since the cancer cells actively grow deviating from the normal growth control, cell proportion in the S period and the $G_2$ period is considered to be large, and the cells are considered to become cancerous in such case. The progression of such cancer can be fast, and thus such cancer can be malignant. Furthermore, heteroploidy is considered to occur when an abnormal M period has elapsed or the cell has advanced to the $G_1$ period without going through the M period and then entered to the S period, and thus, the cell is considered to be malignant when the cell proportion in the M period is small. Therefore, the CDK1 is used as the first CDK and the CDK2 is used as the second CDK, classification to groups is carried out according to the magnitude of the CDK1 specific activity, wherein the CDK2 specific activity value takes a value reflecting the cell ratio in the S period of the groups having a similar CDK1 specific activity. When cells in the S period are in great numbers, the tissue where the cells are configuring cells can be determined as clinically malignant, that is, as a malignant cancer that is likely to metastasize and has poor prognosis.

Therefore, information useful in diagnosing the cancer patient to be examined can be provided by obtaining the first parameter in the malignant tumor of the cancer patient to be examined, such as the specific activity of the first CDK, and the second parameter or the specific activity of the second CDK, and providing information having the first parameter and the second parameter within a sample data extraction range defined based on the first parameter and the second parameter of the malignant tumor of the cancer patient to be examined and being related to the recurrence of the cancer patient administered with the anthracycline anticancer drug.

Information useful in predicting the effectiveness of the anthracycline anticancer drugs in the cancer patient to be examined, in selecting the treatment method for the cancer patient to be examined, and the like can be provided by obtaining the first parameter in the malignant tumor of the cancer patient to be examined, such as the specific activity of the first CDK, and the second parameter or the specific activity of the second CDK, and providing information having the first parameter and the second parameter within a sample data extraction range defined based on the first parameter and the second parameter of the malignant tumor of the cancer patient to be examined and being related to the recurrence, after the malignant tumor is extirpated, of the cancer patient administered with the anthracycline anticancer drug.

[2] Diagnosis Support Device

The diagnosis support device according to one embodiment (first embodiment) of the present invention will be described below. The diagnosis support device according to the present embodiment uses the specific activity of the first CDL as the first parameter and the specific activity of the second CDK as the second parameter.

Specifically, the diagnosis support device according to the first embodiment acquires the expression levels and the activity values of the CDK1 and the CDK2 of the malignant tumor collected from the cancer patient to be examined. The CDK1 specific activity and the CKD2 specific activity are calculated from the expression levels and the activity values of the acquired CDK1 and CDK2. A sample data extraction range is determined based on the calculated CDK1 specific activity and CDK2 specific activity. The device of the first embodiment stores data including sample data in which the first parameter and the second parameter of the malignant tumor collected from the cancer patient administered with the anthracycline anticancer drugs are corresponded to information related to the recurrence of the cancer patient after the malignant tumor is extirpated. The sample data of the patient is extracted from the data stored in advance. Screen information for displaying a screen including the information related to the recurrence contained in the extracted sample data and the information on the cancer patient to be examined on a display device is generated, and the generated screen is allowed to display.

The data stored in advance in the device of the first embodiment contains the sample data. The sample data includes information obtained from a plurality of cancer patients administered with the anthracycline anticancer drugs. Specifically, the first parameter and the second parameter of the malignant tumor collected from the cancer patient are included. Furthermore, information related to the recurrence of the cancer patient after the malignant tumor is extirpated is also included. The information related to the recurrence after the malignant tumor is extirpated specifically includes presence of recurrence of the cancer patient, a number of days from extirpation of the malignant tumor to recurrence (if recurrence has not occurred, a number of days elapsed from the extirpation).

The screen displayed by the display device on the device of the first embodiment includes information related to recurrence contained in the extracted sample data and the information on the cancer patient to be examined. The information related to the recurrence contained in the extracted sample data specifically includes information on the presence of recurrence of the relevant patient. Furthermore, the recurrence rate calculated based on the information on the presence of the recurrence is also included therein. The information on the cancer patient to be examined includes ID number, age, and the like of the cancer patient to be examined. Furthermore, the CDK1 specific activity and the CDK2 specific activity of the malignant tumor of the cancer patient to be examined are also included therein.

Figure 1:
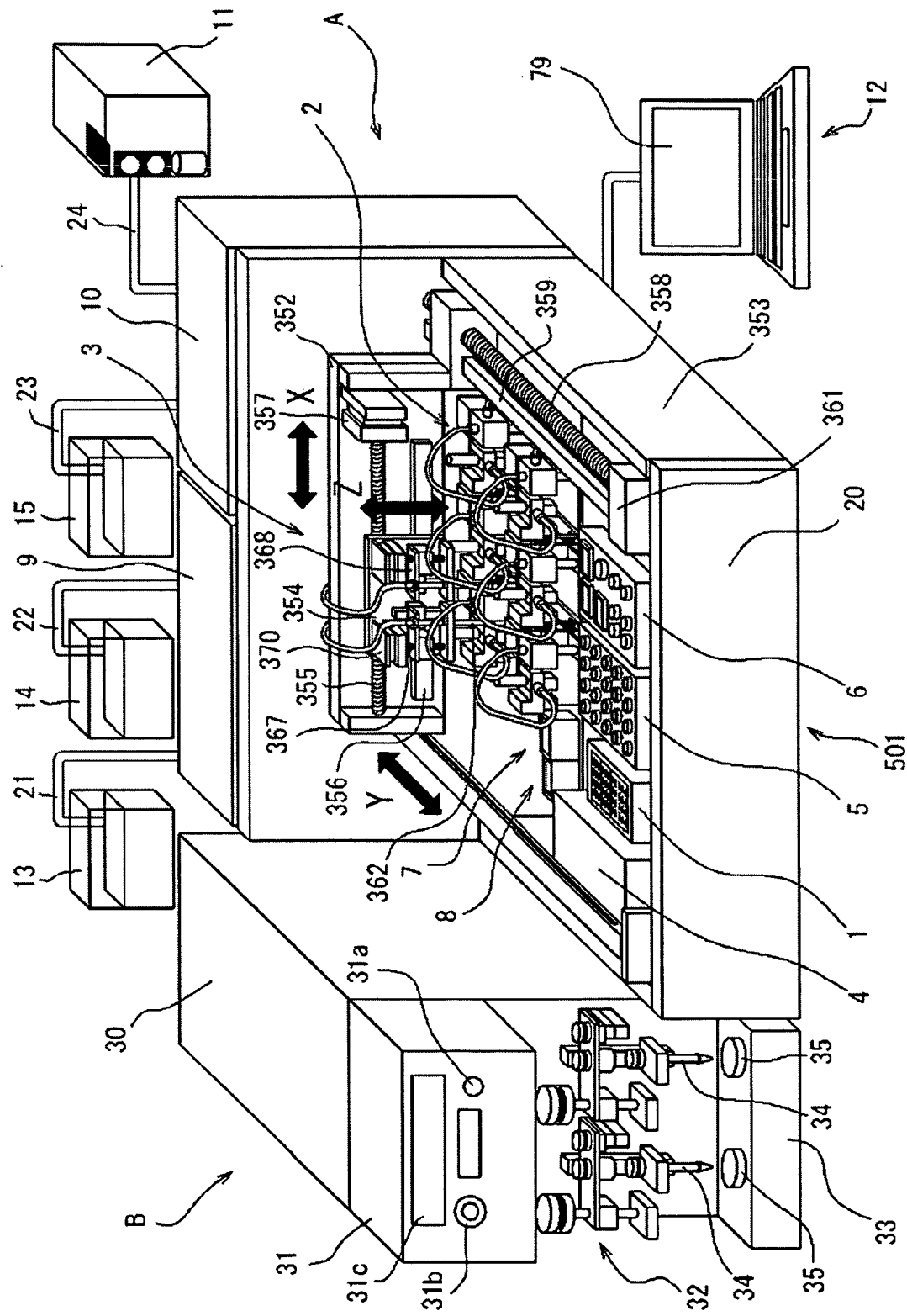
FIG. 1 is a perspective explanatory view of a first embodiment of a device of the present invention.

FIG. 1 is a perspective explanatory view of the first embodiment of the device of the present invention. The diagnosis support device according to the first embodiment is configured by a measuring device A and a solubilizing device B. The measuring device A is configured by a measurement unit 501 and a data processing unit 12. The measuring unit 501 measures the activity value and the expression level of the CDK1 and the activity value and the expression level of the CDK2, and is mainly configured by a detecting member 4 arranged at the front portion of a device body 20; a tip setting member 1; first reagent setting member 5 and second reagent setting member 6; an activity measurement unit 2 arranged at a back portion of the device body 20; a waste bath 7 for accommodating waste liquid and a pipette washing bath 8 for washing pipette; a dispensing mechanism member 3 arranged on the upper side of the device body 20, for moving the pipette in three directions (X direction, Y direction, and Z direction); and a fluid member 9 and a body controller 10 arranged at the back part of the device body 20. The data processing unit 12 is communicably connected to the body controller 10. A pure water tank 13, a washing liquid tank 14, a waste liquid tank 15, and a pneumatic source 11 are arranged in the measuring device A. The pure water tank 13 stores pure water for washing a flow channel at the end of measurement and is connected to the fluid member 9 with a conduit 21; the washing liquid tank 14 stores washing liquid for washing the pipette and is connected to the pipette washing bath 8 with a conduit 22; and the waste liquid tank 15 for accommodating the waste liquid is connected to the waste bath 7 with a conduit 23. The solubilizing device B for obtaining a sample that can be processed in the measuring device A from a biological specimen is arranged next to the measuring A in the diagnosis support device according to the first embodiment.

The solubilizing device B and the measuring device A will be described in order below.

[Solubilizing Device]

The solubilizing device B prepares a liquid sample that can be processed in the measuring device A from the biological specimen of the tissue and the like extirpated from the patient prior to the process by the measuring device A, and is mainly configured by a housing 30, an operating member 31 arranged on the upper side at the front surface of the housing 30, a driving member 32 including a pair of pestles 34 for pressing and grinding the biological specimen, and a sample setting member 33 to be set with an eppen tube 35 accommodating the biological specimen.

The driving member 32 moves the pestles 34 in the up and down direction and provides rotational movement thereto, so that the biological specimen injected into the eppen tube 35 is pressed and grinded. A controller (not shown) for controlling the operation of the driving member 32 is arranged in the housing 30.

An operation button 31a, an operation lamp 31b, and a display part 31c for displaying the state of the device and error message are arranged on the operating member 31. A cooling means (not shown) is arranged in the sample setting member 33 to maintain the biological specimen in the eppen tube (product name) set in a concave area of the upper surface of the sample setting member 33 at a constant temperature.

The supernatant solution of the biological specimen solubilized by the solubilizing device B and subjected to centrifugal process by a centrifugal machine (not shown) is collected to a predetermined sample container and set in the first reagent setting member 5 of the measuring device A.

[First Reagent Setting Member]

A cooling means (not shown) is arranged in the first reagent setting member 5, similar to the sample setting member 33, to maintain the sample, the CDK1 antigen (calibration 1), the CDK2 antigen (calibration 2), the fluorescent labeled CDK1 antibody, the fluorescent labeled CDK2 antibody and the like in the container such as screw cap set in the concave area of the upper surface of the first reagent setting member 5 at a constant temperature. In the first embodiment, a total of 20 concave areas are formed in a matrix of five by four, so that a maximum of 20 containers such as screw cap can be set.

[Second Reagent Setting Member]

The second reagent setting member 6 is arranged next to the first reagent setting member 5. A plurality of concave areas is formed in the second reagent setting member 6, similar to the first reagent setting member 5, and the eppen tube (product name) and the containers such as screw cap with buffer, substrate solution, and fluorescent enhancement reagent are set in these concave areas.

Prior to the process by the measuring device A, a solid phase tip for protein is set in the tip setting member 1, and a column is set in the activity measurement unit 2.

[Tip Setting Member]

Figure 2:
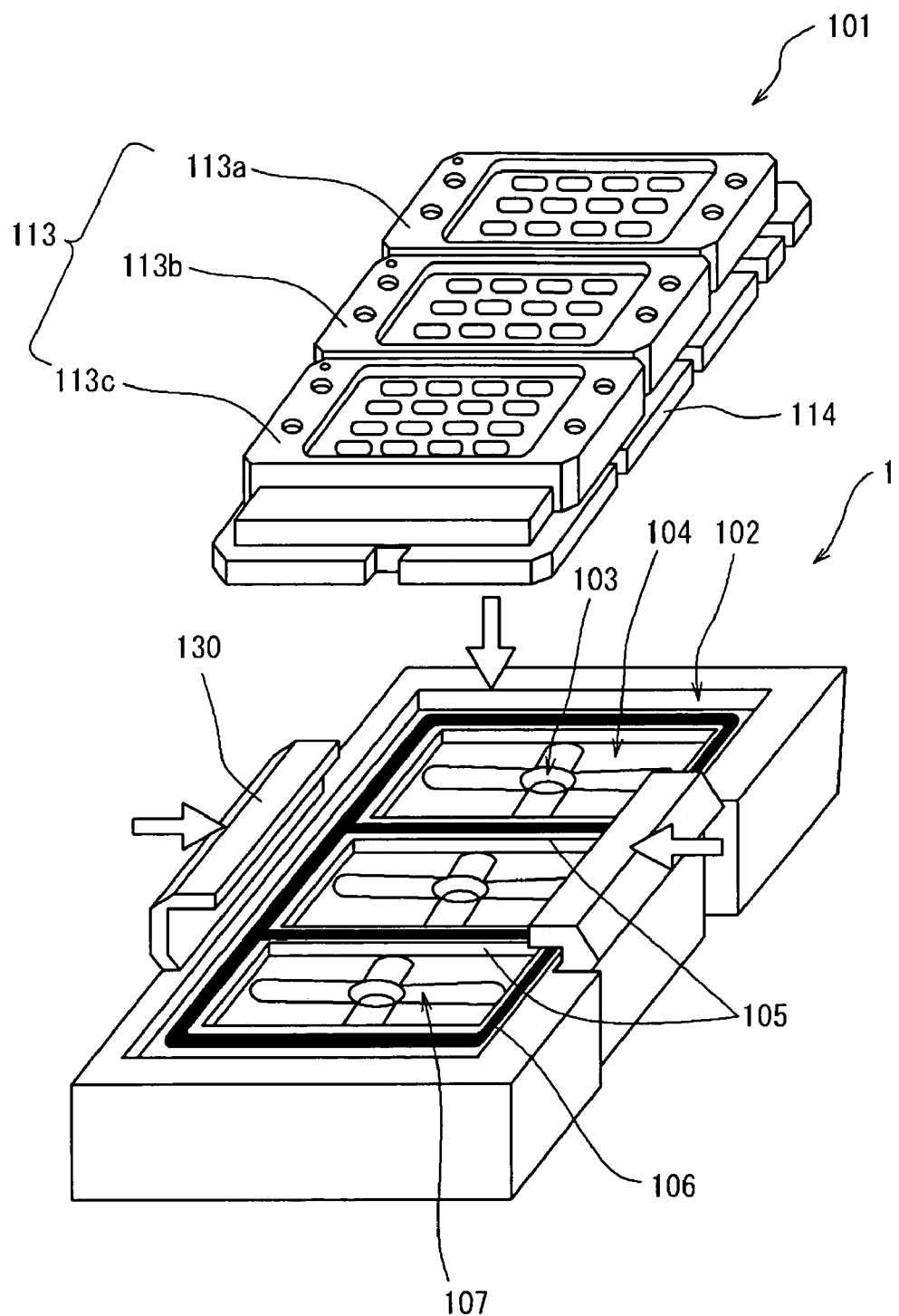
FIG. 2 is a perspective explanatory view of a tip setting member and a solid phase tip for protein in the device shown in FIG. 1.
Figure 3:
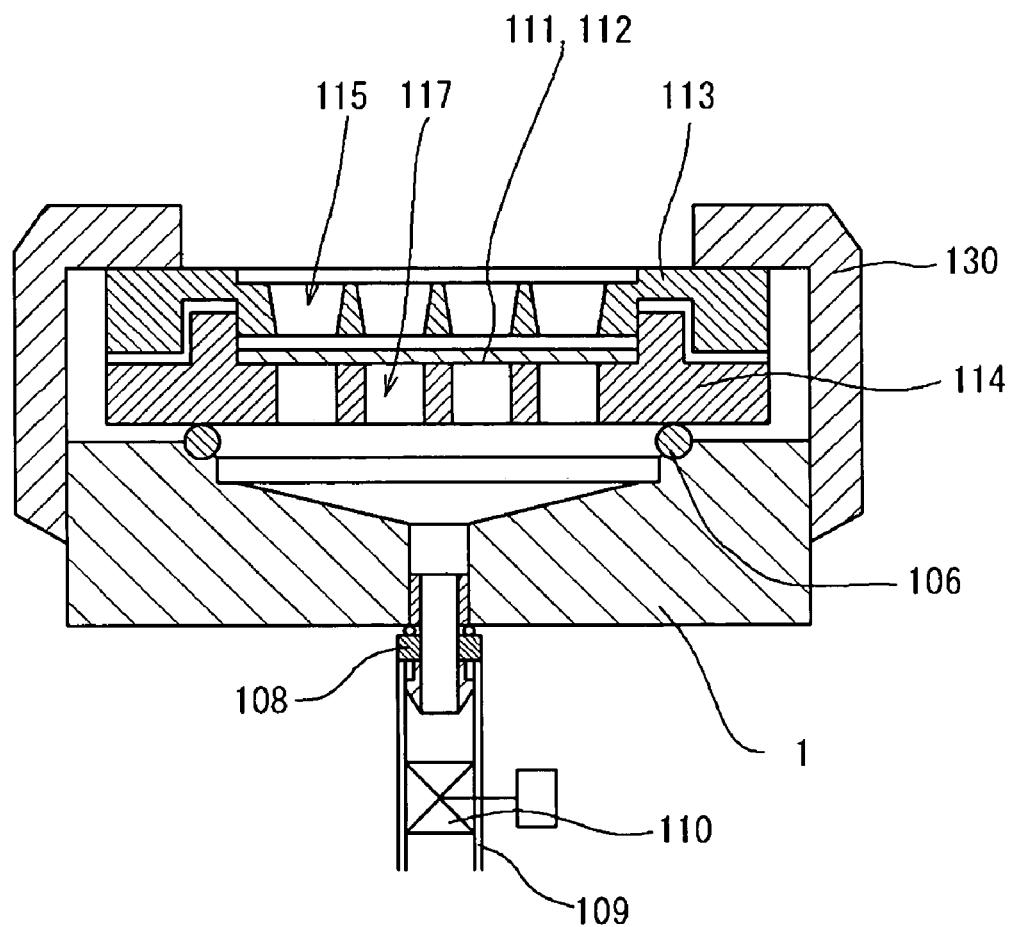
FIG. 3 is a cross sectional explanatory view of the tip setting member and the solid phase tip for protein in the device shown in FIG. 1.

The tip setting member 1 is made up of aluminum blocks, wherein a concave part 102 for mounting the solid phase tip for protein 101 is formed at the upper surface and three aspiration ports 103 are formed at the bottom part, as shown in FIGS. 2 and 3. More specifically, the tip setting member 1 includes a first concave part 102 of rectangular shape at the upper surface, and three second concave parts 104 also of rectangular shape at the bottom part of the first concave part 102. The second concave parts 104 are independent from each other by a partition wall 105 so as to be in a non-communicating state when the solid phase tip for protein 101 is mounted on the tip setting member 1. A rubber elastic gasket 106 of rectangular frame shape is arranged at the peripheral edge of the second concave part 104 at the bottom surface of the first concave part 102.

The second concave part 104 includes a cross-shaped groove 107 at the bottom part and the aspiration port 103 at the center of the bottom part, wherein the groove bottom of the groove 107 is inclined so as to become deeper towards the center from the peripheral edge of the second concave part 104. The aspiration port 103 communicates with a nipple 108 arranged to connect to an external aspiration pneumatic source 11. A tube 109 having one end connected to the aspiration pneumatic source 11 side has the other end connected to the nipple 108. An open/close valve 110 is arranged in the tube 109.

The solid phase tip for protein 101 to be hereinafter described in detail is mounted horizontally at the bottom surface of the first concave part 102 by way of a gasket 106. The aspiration pump is activated after the protein containing specimen solution is injected or dropped into each well of the solid phase tip for protein 101.

The solid phase tip for protein 101 is then air tightly attracted to the bottom surface of the first concave part 102 by way of the gasket 106, and the specimen solution in each well is aspirated through the porous film, to be hereinafter described, whereby the protein to be measured is solid phase formed on the porous film. In FIGS. 2 and 3, 130 is a pressing mechanism for pressing and fixing the solid phase tip for protein 101 to the bottom surface of the first concave part 102. The pressing mechanism 130 is sled in a direction of the arrow in the figure after the solid phase tip for protein 101 is mounted on the first concave part 102, so that the upper part thereof presses the upper surface of the solid phase tip for protein 101 and fixes the same to the first concave part 102.

Figure 4:
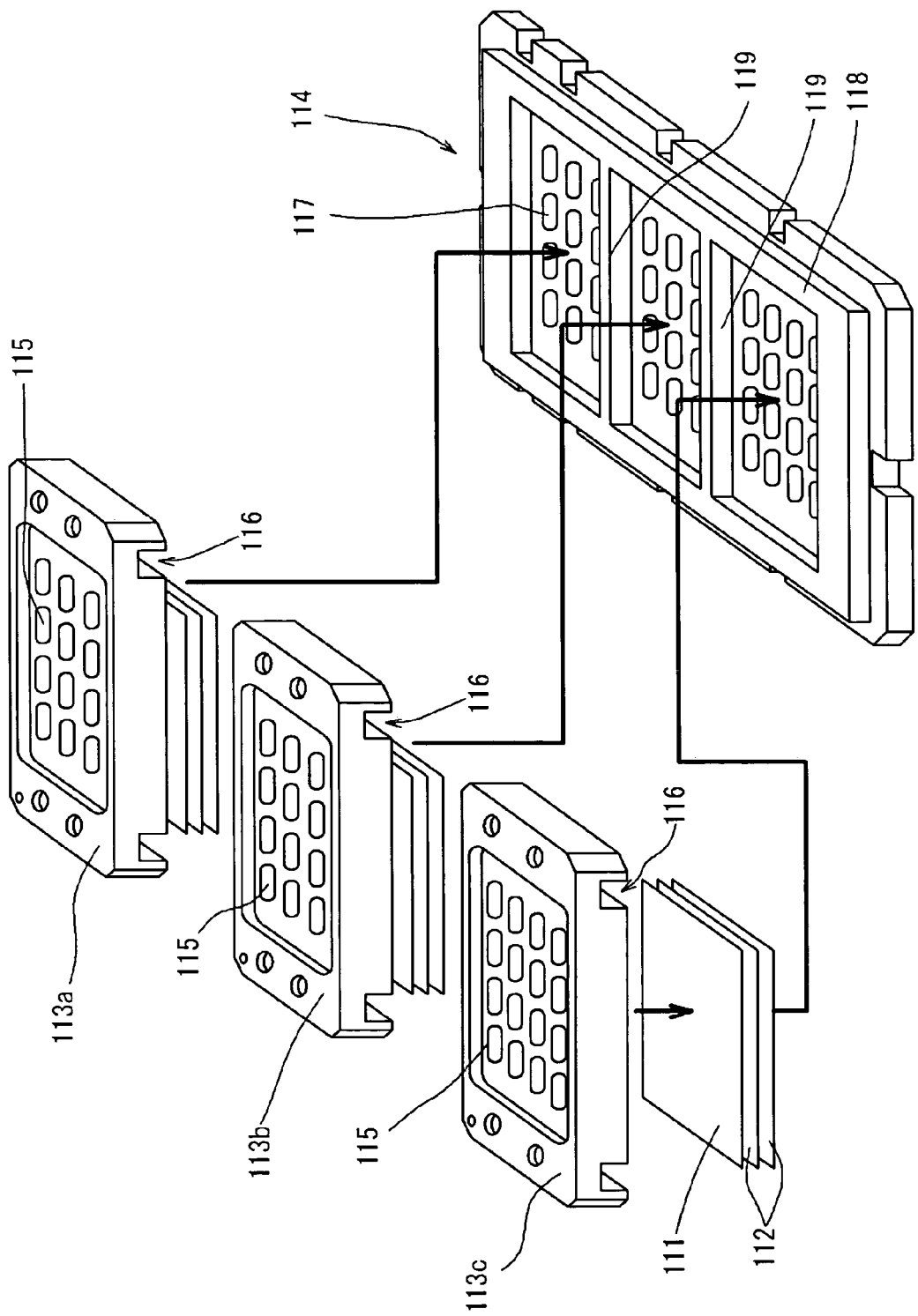
FIG. 4 is an exploded explanatory view of an upper plate and a lower plate of the solid phase tip for protein.
Figure 5:
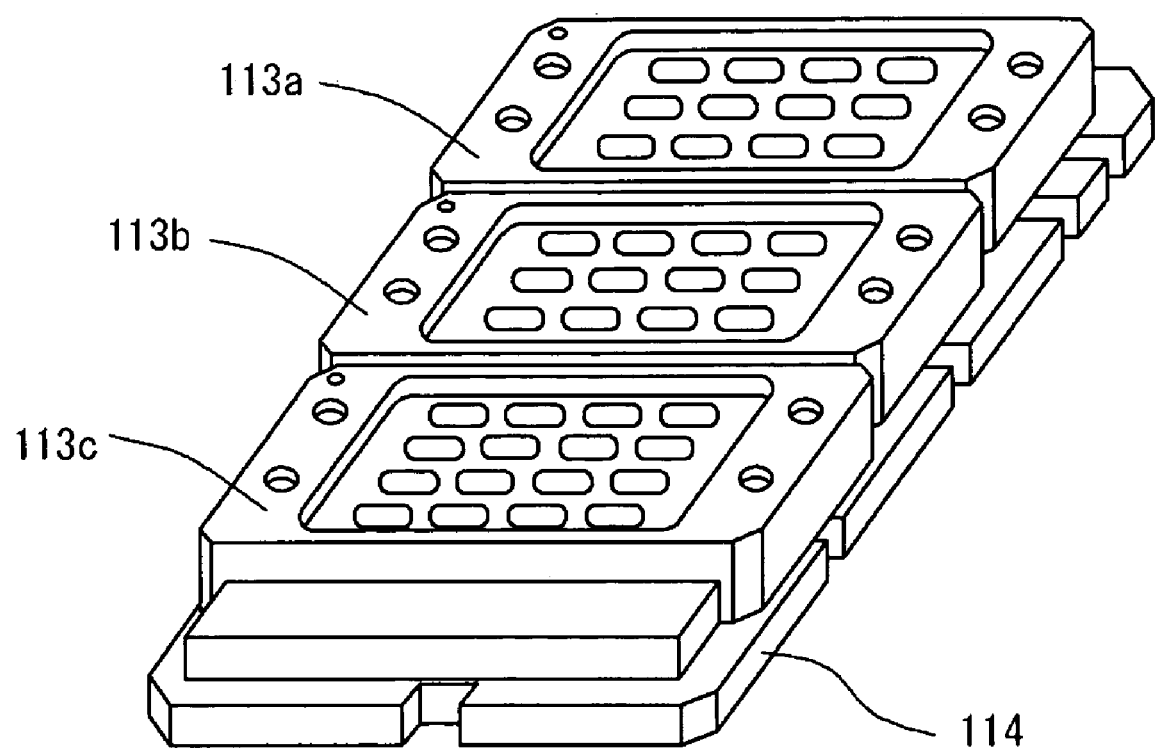
FIG. 5 is a perspective explanatory view of the solid phase tip for protein with the upper plate attached to the lower plate.

As shown in FIGS. 4 and 5, the solid phase tip for protein 101 is configured by a porous film 111 and a filter paper 112, and upper plate 113 and lower plate 114 for sandwiching the porous film 111 and the filter paper 112. The solid phase tip for protein 101 has a function of contacting the antibody solution containing antibody of cyclin-dependent kinase and the biological specimen (sample).

As shown in FIGS. 4 and 5, the upper plate 113 is configured by three plates being independent from each other, that is, a first upper plate 113a, a second upper plate 113b, and a third upper plate 113c. Each upper plate has a rectangular plate shape, wherein the first upper plate 113a and the second upper plate 113b are both formed with twelve oval through holes 115 arrayed in a matrix form of four by three, and the third upper plate 113c is formed with sixteen oval through holes 115 arrayed in a matrix form of four by four. Each upper plate includes a region, which is independent from each other for specimen processing, formed with a plurality of through holes. A groove 116 is formed along a short side at the bottom surface of each upper plate.

A total of forty oval through holes 117 arrayed in a matrix form is formed in the lower plate 114 having a rectangular plate shape at positions corresponding to each through hole 115 of the upper plates 113a, 113b, 113c. The through holes 117 have the same shape and cross sectional area as the through holes 115. The lower plate 114 has a region formed with a plurality of through holes corresponding to each region of the upper plates 113a, 113b, 113c.

A rib-shaped convex part 118 that goes around the periphery of the forty through holes 117 once, and a partition wall 119 for partitioning the through holes 117 to three regions in correspondence to each region of the upper plate 113a, 113b, 113c are formed on the upper surface of the lower plate 114. Three rectangular porous film installing regions are partitioned on the inner side by the convex part 118 and the partition wall 119. The upper plate 113 and the lower plate 114 may be made of vinyl chloride resin and the like.

As shown in FIGS. 2 to 5, a stacked body including the porous film 111 and the filter paper (filter) 112 is mounted on the porous film installing region of the lower plate 114, and the grooves 116 of each upper plate 113a, 113b, 113c are sequentially fitted to the corresponding convex part 118 of the lower plate 114, so that the upper plates 113a, 113b, 113c are attached to the lower plate 114 thereby forming the solid phase tip for protein 101. Each through hole 115 and each through hole 117 then become coaxial to each other.

The solid phase tip for protein described above has the upper plate divided into three regions, so that three regions can be aspirated independently, but the number of upper plates may be two, or four or more, and is not particularly limited in the present invention. The number of upper plates is appropriately selected in view of the number of measurement items and the number of samples.

[Activity Measurement Specimen Preparation Unit]

As shown in FIGS. 6 to 10, the activity measurement specimen preparation unit 2 includes a plurality of specimen preparation members 211 each including a column 201 and a fluid manifold 213, and is used to measure the activity value of the CDK.

Figure 6:
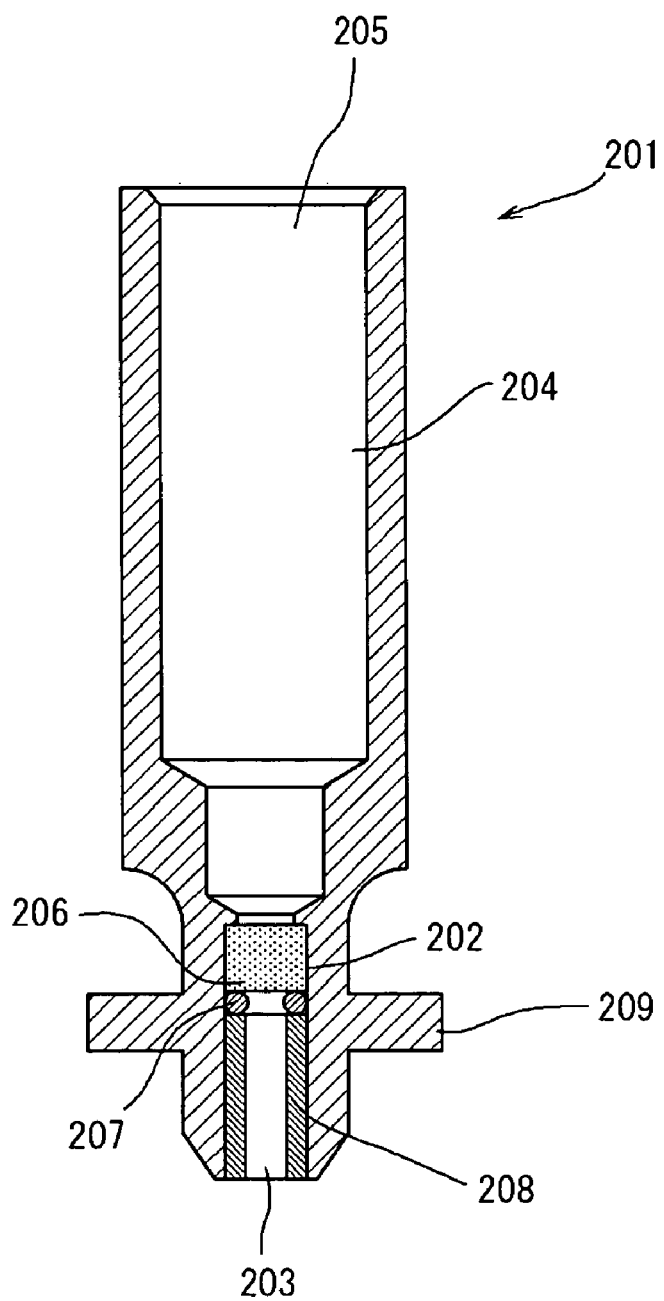
FIG. 6 is a cross sectional explanatory view of a column of a specimen preparation member of an activity measurement unit in the device shown in FIG. 1.

The column 201 shown in FIG. 6 is made of a cylindrical body made of vinyl chloride resin, and includes therein a carrier holding member 202 for holding a carrier 206 used to isolate the target substance in the liquid specimen, and a liquid storage member 204 for receiving and storing the liquid specimen to introduce the liquid specimen to the carrier holding member 202. The column 201 has an opening 205 through which the liquid sample can be externally injected or from which the liquid specimen can be collected from the outside at the upper part of the liquid storage member 204, and includes a connection flow channel 203 for introducing the liquid specimen to the fluid manifold 213 to the lower part of the carrier holding member 202 and receiving the liquid specimen from the fluid manifold 213. The column 201 configures a means for contacting the substrate solution containing a predetermined substrate and the biological specimen (sample).

The carrier 206 is made of monolithic silica gel of circular cylinder shape, wherein the monolithic silica gel has a configuration in which the three-dimensional network frame work and the clearance thereof are integrated, unlike to the particle carrier. The predetermined CDK antibody is immobilized to the monolithic silica gel. The carrier 206 is inserted to the carrier holding member 202 from the lower opening of the column 201, and is elastically pushed and supported by a fixing pipe 208 by way of an O-ring 207. The fixing pipe 208 is press-fit from the lower opening of the column 201, wherein the fixing pipe 208 and the hole of the O-ring 207 form the connection flow channel 203.

A mounting flange 209 for mounting and fixing the column 201 to the specimen preparation member 211 is formed at the lower end of the column 201. The flange 209 is an oval flange formed by cutting out both sides of a disc shaped flange having a diameter D in parallel so as to have a width W (W<D).

Figure 7:
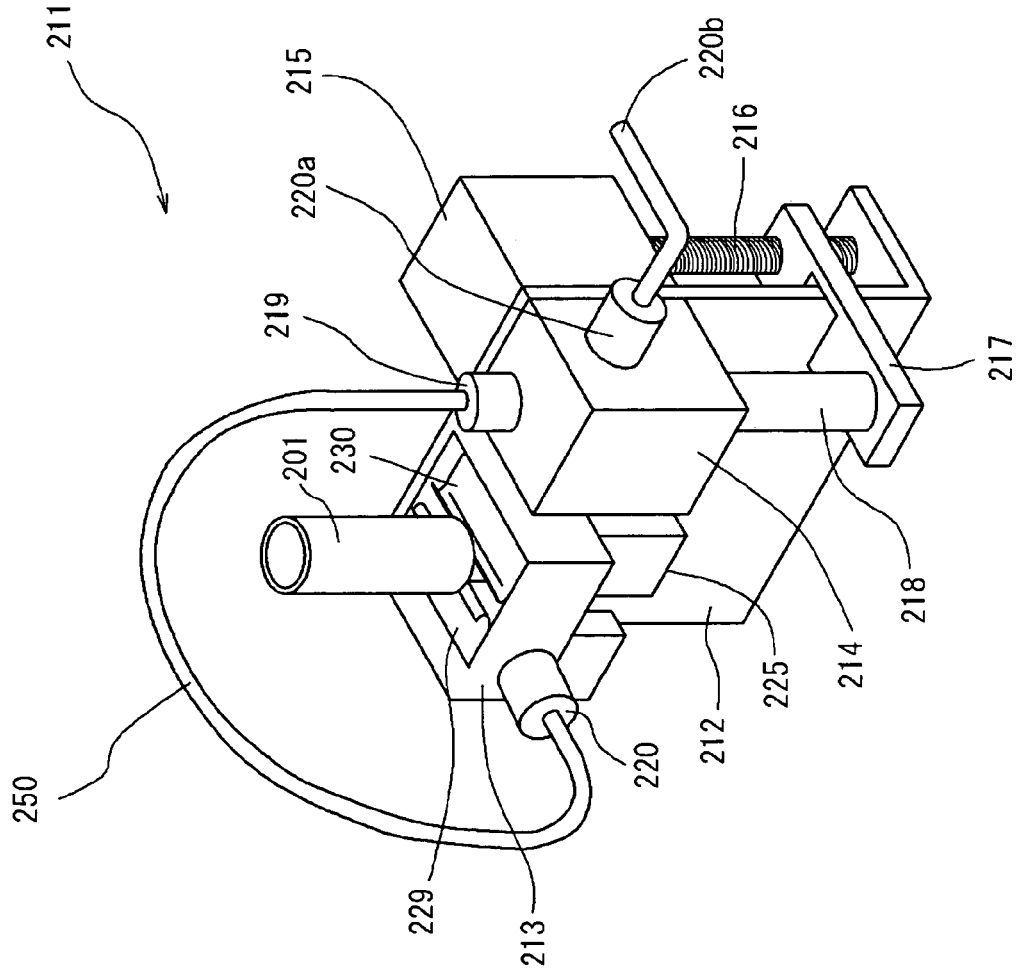
FIG. 7 is a perspective view of the specimen preparation member of the activity measurement unit in the device shown in FIG. 1.

FIG. 7 is a perspective explanatory view of the specimen preparation member of the activity measurement unit in the device of FIG. 1. As shown in FIG. 7, the specimen preparation member 211 includes an L-shaped supporting plate 212, and the fluid manifold 213, a syringe pump 214, and a stepping motor with reducer 215 are fixed on the supporting plate 212.

A screw shaft 216 is connected to the output shaft of the stepping motor 215. A drive arm 217 to be screwed to the screw shaft 216 is connected to the distal end of a piston 218 of the syringe pump 214. The piston 218 moves up and down when the screw shaft 216 is rotated by the stepping motor 215. The syringe pump 214 and the fluid manifold 213 are connected to a liquid feeding tube 250 by way of connectors 219, 220. The syringe pump 214 is connected to a chamber 234 (see FIG. 10) accommodating fluid (washing liquid) for filling the flow channel by a liquid feeding tube 220b by way of a connector 220a.

Figure 8:
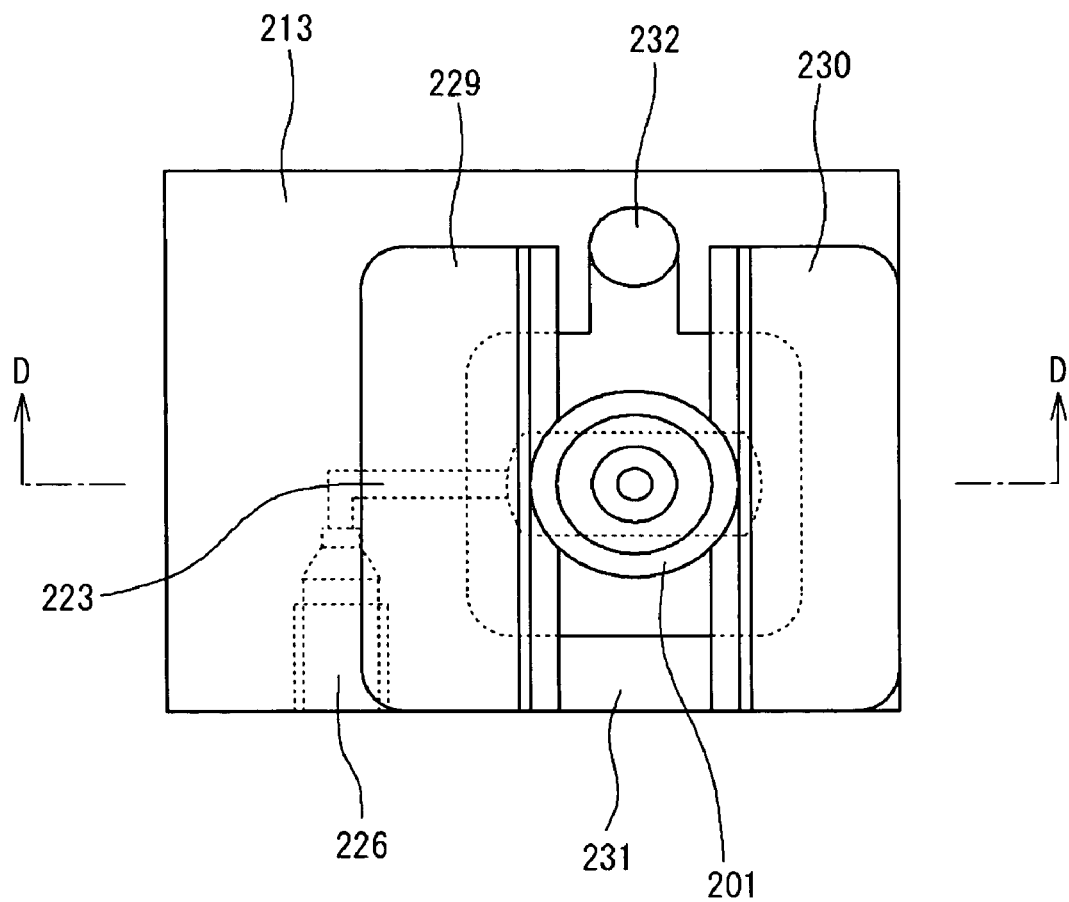
FIG. 8 is a top view of a fluid manifold of the specimen preparation member shown in FIG. 7.
Figure 9:
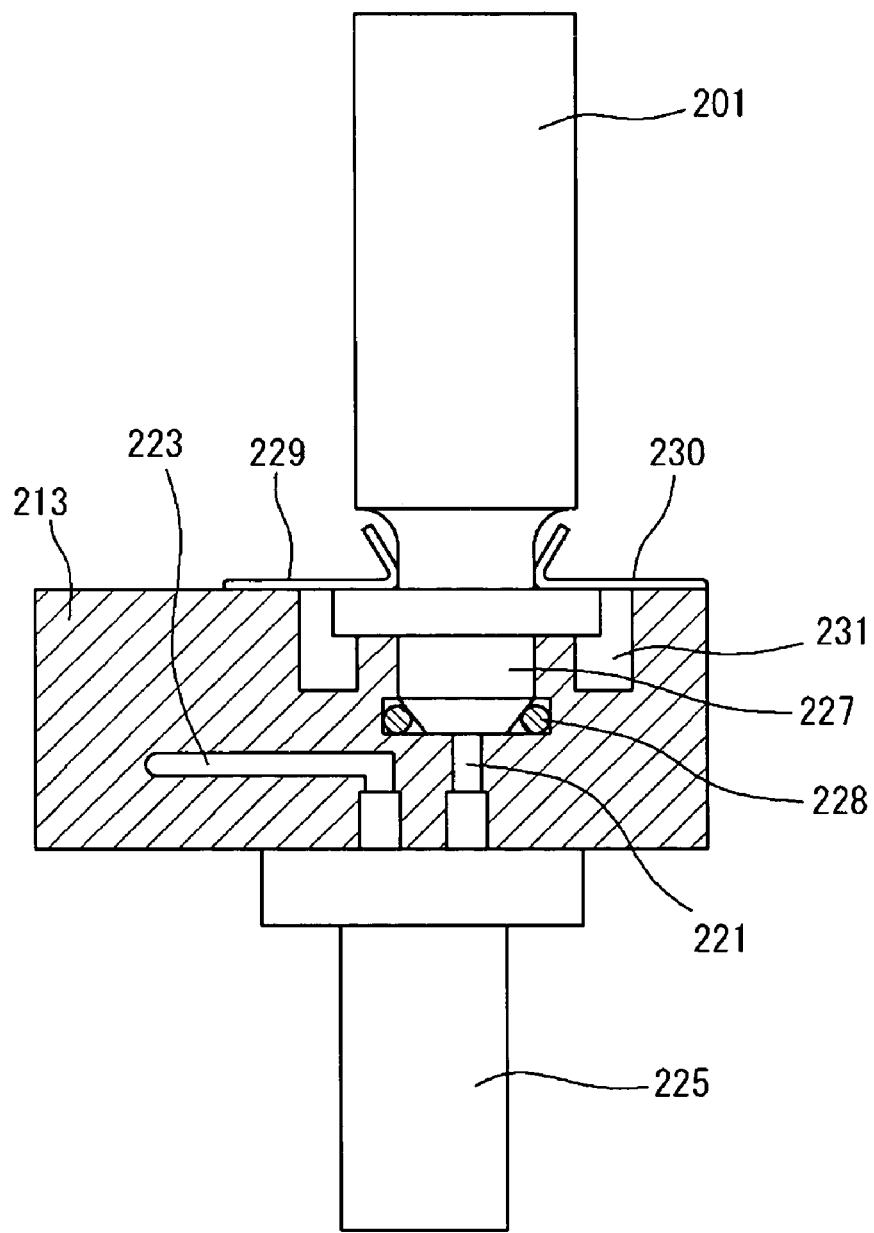
FIG. 9 is a cross sectional view taken along line D-D of FIG. 8.

As shown in FIGS. 8 and 9, the fluid manifold 213 includes a column connecting part 221 to which the lower opening of the column 201 is connected.

The fluid manifold 213 includes a flow channel 223 therein, and has an electromagnetic valve 225 for opening/closing the flow channel 223 and the column connecting part 221 on the lower surface. The fluid manifold 213 has a connector connection screw hole 226 for connecting a connector 220 on the side surface, which screw hole 226 is connected to the flow channel 223.

Figure 10:
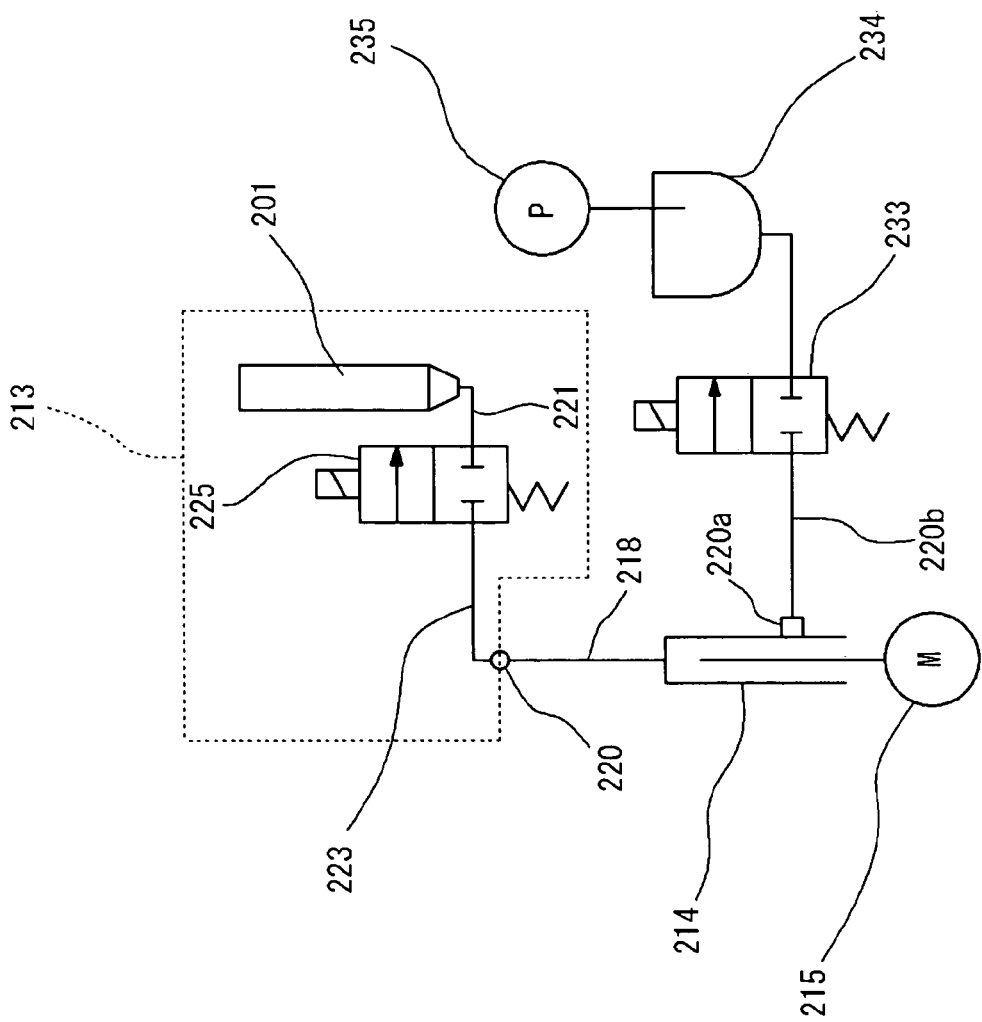
FIG. 10 is a fluid circuit diagram of the specimen preparation member shown in FIG. 7.

FIG. 10 is a fluid circuit diagram of the specimen preparation member shown in FIG. 7. FIG. 10 shows a state in which the syringe pump 214 is connected to the fluid manifold 213 by way of the connector 220. A chamber 234 is connected to the syringe pump 214 by way of the electromagnetic valve 233, and positive pressure is applied to the chamber 234 from a positive pressure source 235.

A method of mounting the column 201 to the fluid manifold 213 will be now described.

As shown in FIGS. 8 to 10, a column mounting concave part 227 for receiving the lower end of the column 201 is formed on the upper surface of the fluid manifold 213, the center of the bottom part of the concave part 227 passes through the column connecting part 221, and an O-ring 228 is attached to the circumference of the bottom part. Two pressing plates 229, 230 having a cross section of L-shape are fixed in parallel on the upper surface of the fluid manifold 213 at an interval wider than the width W and narrower than D with the column mounting concave part 227 as the center.

In order to prevent sample or reagent that has passed the carrier 206 inside the column 201 fixed to the fluid manifold 213 from contacting fluid (washing liquid) that fills the flow channel 223 inside the fluid manifold 213 and being diluted, the electromagnetic valve 225 is opened (electromagnetic valve 233 is closed) before the column 201 is fixed to the column mounting concave part 227 and the syringe pump 214 is aspiration operated only by about 16 μL. The liquid level of the column connecting part 221 thereby lowers and an air gap forms.

Subsequently, the column 201 is mounted to column mounting concave part 227 so that the flange 209 passes between the pressing plates 229, 230, and then rotated clockwise or counterclockwise by 90 degrees. The portion of the diameter D of the flange 209 engages the pressing plates 229, 230, and the flange 209 is fixed by the pressing plates 229, 230 due to the elasticity of the O-ring 228. When removing the column 201, the column 201 is rotated either to the left or the right by 90 degrees while being pushed.

When the column 201 is mounted to fluid manifold 213 of the specimen preparation unit 211, the concave part 227 of the fluid manifold 213 is filled with manually or automatically dispensed fluid in order to prevent air bubbles from mixing, but the fluid flows out from increase in volume when the distal end of the column 201 is inserted to the concave part 227. An overflow liquid storage concave part 231 is arranged at the periphery of the column mounting concave part 227 in order to prevent the fluid from flowing out to the periphery, and an overflow liquid discharging concave part 232 for aspirating and discharging the overflow liquid by pipette is arranged at one part of the overflow liquid storage concave part 231.

Various samples and reagents are injected or aspirated to or from a predetermined location by the dispensing mechanism member 3 equipped with the pipette.

The operation of the upper opening 205 of the column 201 in a case where the sample or the reagent is injected will be now described. The electromagnetic valve 225 is first opened (electromagnetic valve 233 is closed), and the syringe pump performs the aspirating operation when the sample or the reagent is injected to the opening 205. The air gap and the sample or the reagent are then passed through the electromagnetic valve 225, and then aspirated to the syringe pump side. The syringe pump then performs ejecting operation. The sample or the reagent is then passed through the electromagnetic valve 225, and sent to the column 201.

[Dispensing Mechanism Member]

As shown in FIG. 1, the dispensing mechanism member 3 includes a frame 352 for moving the pipette in the X direction, a frame 353 for moving the pipette in the Y direction, and a plate 354 for moving the pipette in the Z direction.

The frame 352 includes a screw shaft 355 for moving the plate 354 in the direction of the arrow X, a guide bar 356 for supporting and slidably moving the plate 354, and a stepping motor 357 for rotating the screw shaft 355.

The frame 353 includes a screw shaft 358 for moving the plate 352 in the direction of the arrow Y, a guide bar 359 for supporting and slidably moving the frame 352, and a stepping motor 361 for rotating the screw shaft 358.

The plate 354 includes a screw shaft 367 for moving an arm 368 supporting the pipette 362 in the direction of the arrow Z, a guide bar for supporting and slidably moving the arm 368, and a stepping motor 370 for rotating the screw shaft 367.

In the first embodiment, since the dispensing mechanism member 3 is equipped with a pair of pipettes 362, reagent and the like can be simultaneously injected to two sample containers and content can be simultaneously aspirated from two sample containers, whereby the measuring process can be efficiently performed.

[Fluid Member]

As shown in FIG. 1, a fluid member 9, connected to the pipette washing bath 8 for washing the pipette 362 and each specimen preparation member 211, for operating the fluid is arranged at the rear part of the device body 20. As shown in FIG. 10, the fluid member 9 includes an electromagnetic valve 225 of each specimen preparation member 211, an electromagnetic valve 233 for controlling the fluid when filling the liquid from the washing liquid chamber to the syringe 214, an electromagnetic valve for controlling fluid when aspirating and ejecting the liquid with the pipette 362, an electromagnetic valve for controlling the fluid when aspirating the liquid wasted from the pipette 362 in the waste bath 7, and an electromagnetic valve for controlling the fluid when washing the pipette 362 in the pipette washing bath 8.

[Detecting Member]

The detecting member 4 is provided to measure the fluorescence quantity based on the bound fluorescent labeled substance reflecting the protein quantity and the fluorescence quantity based on the fluorescent labeled substance reflecting the amount of phosphate group captured at the porous film 111 of the solid phase tip for protein 101, wherein excitation light is irradiated on the solid phase tip for protein 101, the generated fluorescence is detected, and the electric signal having a magnitude corresponding to the intensity of the detected fluorescence is output to the body controller 10. A generally used detecting member configured by light source unit, illumination system, and light receiving system can be appropriately adopted for the detecting member 4.

[Data Processing Unit]

Figure 11:
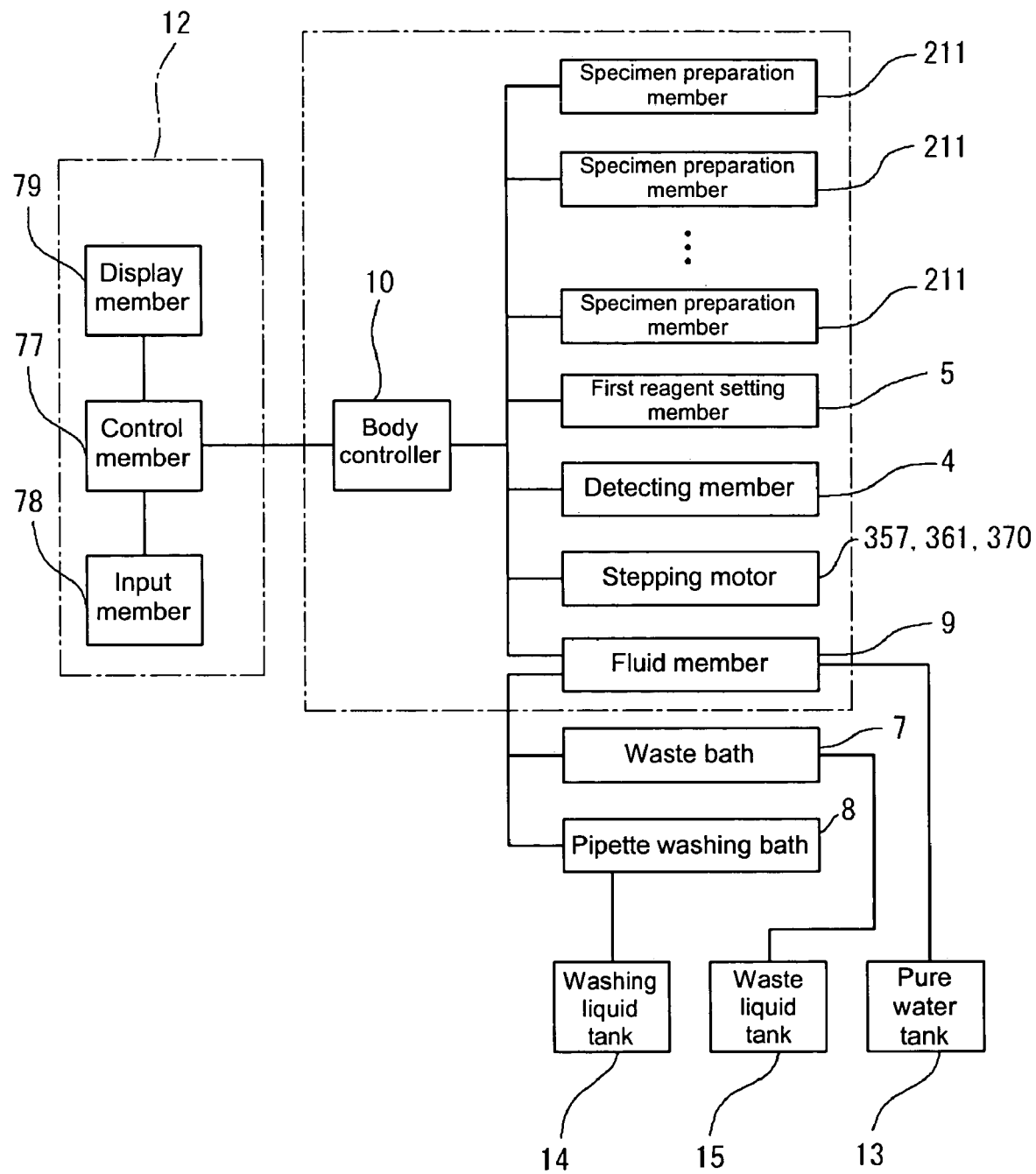
FIG. 11 is a block diagram showing a partial configuration of the device (control system for controlling the device) of the present invention.

FIG. 11 is a block diagram showing a partial configuration (control system for controlling the device) of the device of the first embodiment. As shown in FIG. 1, the data processing unit 12 or the personal computer includes a control member 77, an input member 78, and a display member 79.

The control member 77 has a function of transmitting an operation start signal of the device to the body controller 10 to be hereinafter described. When a command to start operation is transmitted from the control member 77, the body controller 10 outputs a drive signal for driving the stepping motor 215 of each specimen preparation member 211, a drive signal for adjusting the temperature of the first reagent setting member 5, a drive signal for driving the stepping motors 357, 361, 370, and a drive signal for driving the electromagnetic valve in the fluid member 9. The control member 77 further has a function for analyzing the detection result obtained in the detecting member 4.

The detection result obtained in the detecting member 4 is transmitted to the body controller 10. The body controller 10 transmits the detection result obtained in the detecting member 4 to the control member 77.

The display member 79 is arranged to display result of analysis and the like obtained in the control member 77.

Figure 12:
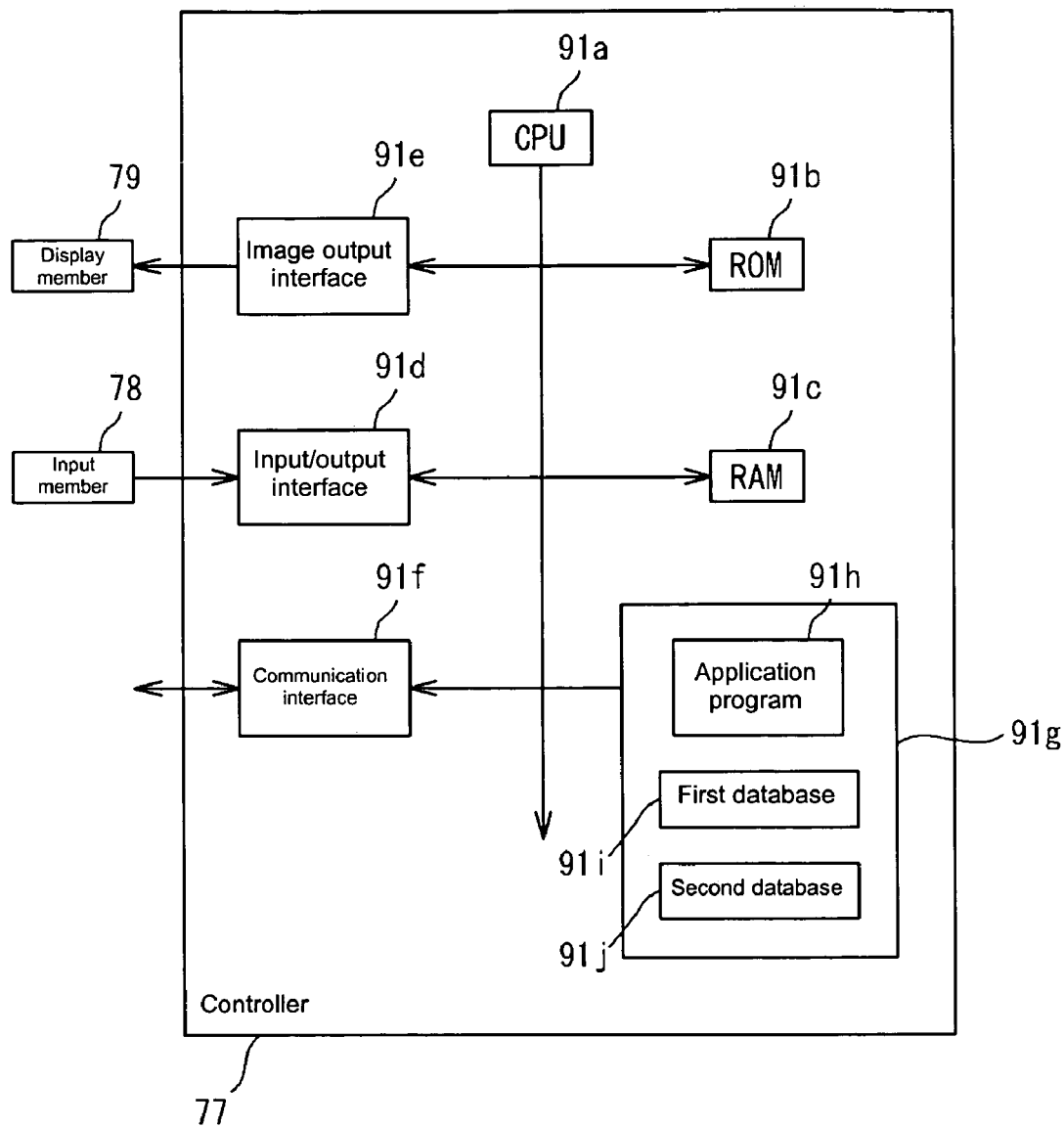
FIG. 12 is a block diagram showing a hardware configuration of a data processing unit.

The configuration of the personal computer used as the data processing unit 12 will be now described in detail. As shown in FIG. 12, the control member 77 is mainly configured by a CPU 91a, a ROM 91b, a RAM 91c, an input/output interface 91d, an image output interface 91e, a communication interface 91f, and a hard disc 91g. The CPU 91a, the ROM 91b, the RAM 91c, the input/output interface 91d, the image output interface 91e, the communication interface 91f, and the hard disc 91g are connected with an electric signal line (bus) so as to communicate electrical signals.

The CPU 91a can execute computer programs stored in the ROM 91b and the computer programs loaded in the RAM 91c. The personal computer can serve as the data processing unit 12 when the CPU 91a executes the application program 91h, as hereinafter described, and executes the operations to be hereinafter described.

The ROM 91b is configured by mask ROM, PROM, EPROM, EEPROM, and the like, and is recorded with computer programs to be executed by the CPU 91a, data used for the same, and the like.

The RAM 91c is configured by SRAM, DRAM, and the like. The RAM 91c is used to read out the computer programs recorded on the ROM 91b and the hard disc 91g. The RAM 91c is used as a work region of the CPU 91a when executing these computer programs.

Various computer programs to be executed by the CPU 91a such as operating system and application program, as well as data used in executing the computer program are installed in the hard disc 91g. A predetermined application program 91h is also installed in the hard disc 91g. The predetermined application program is a program for acquiring the expression levels and the activity values of the CDK 1 and the CDK 2 from the malignant tumor of the cancer patient to be examined, calculating the CDK 1 specific activity and the CDK 2 specific activity from the acquired expression levels and the activity values of the CDK 1 and the CDK 2, determining a sample data extraction range based on the calculated CDK 1 specific activity and CDK 2 specific activity, extracting sample data having the CDK 1 specific activity and the CDK 2 specific activity within the determined range and of the cancer patient administered with anthracycline anticancer drug (such cancer patient is hereinafter referred to as "relevant patient"), calculating the recurrence rate based on the information related to recurrence contained in the extracted sample data, generating a screen including the calculated recurrence rate and the information on the cancer patient to be examined based on the presence of recurrence contained in the information related to the recurrence and the information related to the recurrence, and displaying the generated screen on the display member 79.

In order to acquire the expression level and the activity value, the hard disc 91g includes a first database 91i for storing a standard curve or conversion data for converting fluorescence intensity to expression level or activity value.

The standard curve may be obtained for every measurement of the expression level or the activity value. The first database 91i of the hard disc 91g stores data to use in the calculation for determining the sample data extraction range, data of default value of the sample data extraction range, and data of a set value of the sample data extraction range input and used in the past. The first database 91i of the hard disc 91g also stores information related to recurrence.

The hard disc 91g includes a second database 91j for storing sample data in which the measurement value such as the activity value and the expression level of great number of cancer patients and the clinical information such as presence/absence of recurrence, a number of days from the extirpation of the malignant tumor to the recurrence occurred (if recurrence did not occur, a number of days elapsed after extirpation), information related to postsurgical treatment such as administration of anthracycline anticancer drug and hormone treatment, information related to living body and the like of the relevant cancer patient are corresponded to each other.

Operating system providing graphical user interface environment such as Windows (registered trademark) manufactured and sold by US Microsoft Co. is installed in the hard disc 91g. In the following description, the application program 91h according to the first embodiment is assumed to operate on the operating system.

The input/output interface 91d is configured by serial interface such as USB, IEEE1394, RS-232C; parallel interface such as SCSI, IDE, IEEE1284; analog interface such as D/A converter, A/D converter, and the like. The input member 78 such as keyboard and mouse is connected to the input/output interface 91d, so that the user can input data to the data processing unit 12 by using the input member 78.

The communication interface 91f is, for example, Ethernet (registered trademark) interface. The data processing unit 12 transmits and receives data with the body controller 10 by using a predetermined communication protocol by means of the communication interface 91f.

The image output interface 91e is connected to the display member 79 configured by LCD, CRT, or the like, and is configured to output an image signal corresponding to the image data provided from the CPU 91a to the display member 79. The display member 79 displays the image (screen) according to the input image signal.

[Body Controller]

The body controller 10, connected to each specimen preparation member 211, the detecting member 4, the stepping motors 357, 361, 370, the fluid member 9 and the like, for controlling the same is arranged at a back part of the device body 20.

Figure 13:
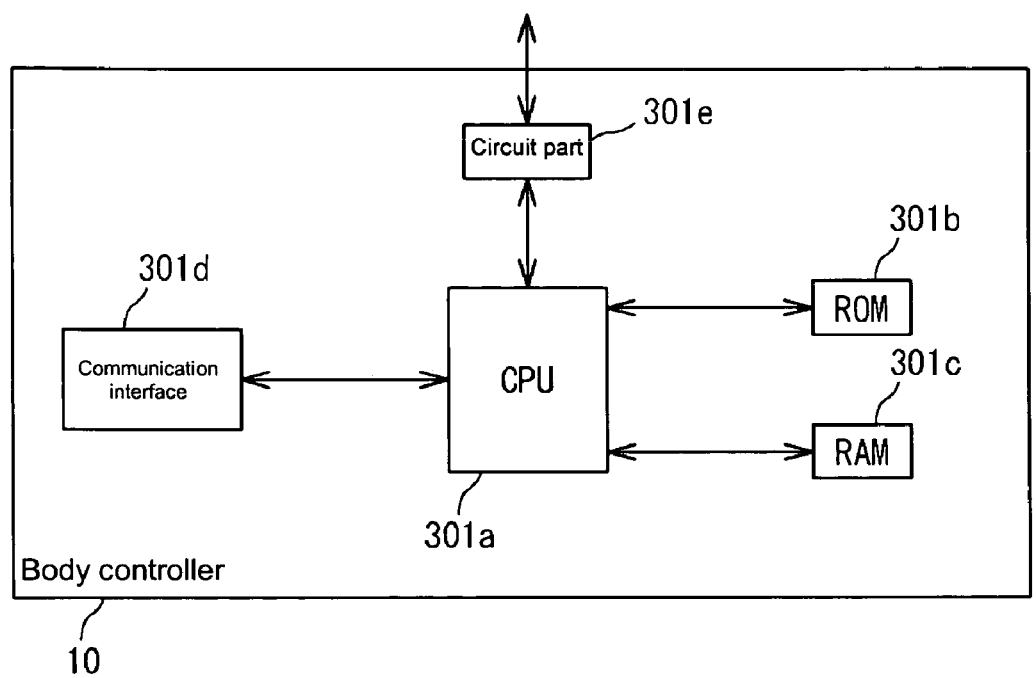
FIG. 13 is a block diagram showing a hardware configuration of a body controller.

As shown in FIG. 13, the body controller 10 includes a CPU 301a, a ROM 301b, a RAM 301c, a communication interface 301d, and a circuit part 301e.

The CPU 301a can execute computer programs stored in the ROM 301b and the computer programs read out in the RAM 301c.

The ROM 301b stores a computer program to be executed by the CPU 301a, data used in the execution of the computer program, and the like.

The RAM 301c is used in reading out the computer program stored in the ROM 301b. The RAM 301c is used as a work region of the CPU 301a when executing these computer programs.

The communication interface 301d is, for example, Ethernet (registered trademark) interface. The body controller 10 can transmit and receive data with the data processing unit 12 by using a predetermined communication protocol by means of the communication interface 301d.

The circuit part 301e includes a plurality of drive circuits and a signal processing circuit (not shown). The drive circuit is arranged in correspondence to the specimen preparation member 211, the first reagent setting member 5, the detecting member 4, the stepping motors 357, 361, 370, and the fluid member 9. Each drive circuit generates a control signal (drive signal) for controlling the corresponding unit (specimen preparation member 211 if drive circuit corresponding to the specimen preparation member 211) according to the instruction data provided from the CPU 301a, and transmits the control signal to the unit. The output signal of the sensor arranged in the unit is provided to the drive circuit, wherein the drive circuit converts the output signal to a digital signal and provides the same to the CPU 301a. The CPU 301a generates the instruction data based on the provided output signal of the sensor.

The signal processing circuit is connected to the detecting member 4. A detection signal indicating fluorescence intensity is output from the detecting member 4, and such detection signal is provided to the signal processing circuit. The signal processing circuit executes signal processing such as noise removal process, amplification process, and A/D conversion process on the detection signal. The data on the detection result obtained as a result of the signal processing is provided to the CPU 301a.

[3] Diagnosis Support of Cancer

The operation of the diagnosis support system according to the first embodiment will be described.

(1) Pre-Process by Solubilizing Device B

Prior to the process by the measuring device A, liquid sample is collected from the tissue containing the malignant tumor extirpated from a cancer patient by using the solubilizing device B. In the procedure thereof, the tissue is first placed in the eppen tube (product name) with a pin set. The eppen tube (product name) is then set in the sample setting member 33 of the solubilizing device B shown in FIG. 1, and the start button of the operating member 31 is pushed, whereby the pestle 34 lowers to a predetermined position and pushes the tissue in the eppen tube (product name) against the bottom of the eppen tube (product name).

Solubilizing liquid such as buffer solution containing surfactant and proteolysis enzyme inhibitor agent and the like is automatically or manually injected into the eppen tube (product name) in such state. Thereafter, the tissue is grinded by the rotation of the pestle 34. The drive of the pestle 34 is stopped after a predetermined time has elapsed, the pestle 34 is moved upward, and thereafter, the eppen tube (product name) is taken out from the sample setting member 33. The solubilized content in the eppen tube (product name) is then set in the centrifugal machine, and the obtained supernatant solution is manually collected as a sample.

(2) Setting of Sample and the Like to the Measuring Device A

The supernatant solution is placed in two sample containers and diluted at dilution ratio different from each other, and thereafter, the sample containers are set at predetermined positions in the first reagent setting member 5. Of the two samples, one is the sample for expression level measurement, and the other is the sample for activity value measurement.

The solid phase tip for protein 101 is set in the tip setting member 1, and eight columns 201 are respectively set in the specimen preparation member 211 of the activity measurement unit 2.

(3) Overall Flow of Process by Device

Figure 15:
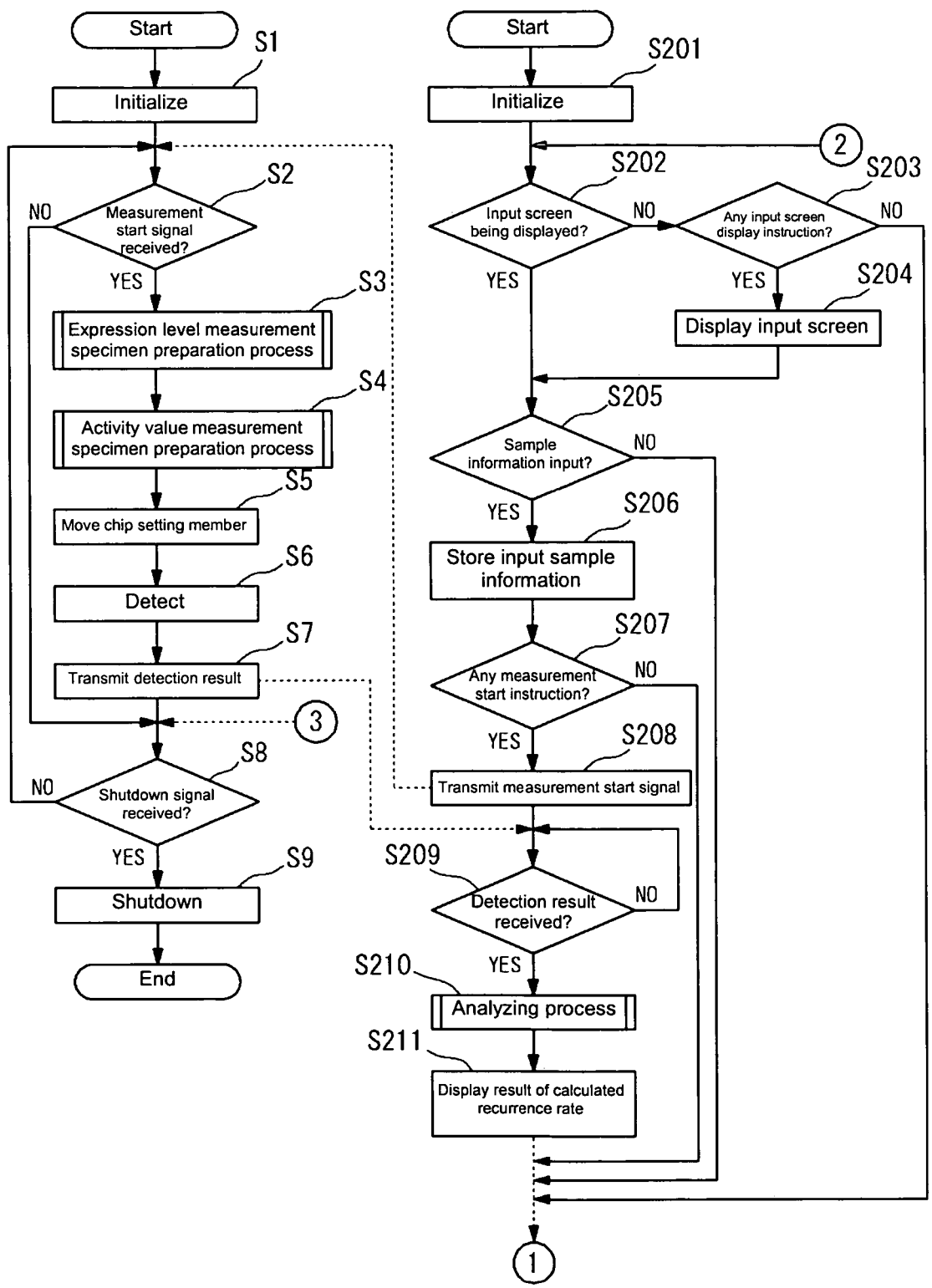
FIG. 15 is a view showing an overall flow of one example of a process by the device.
Figure 16:
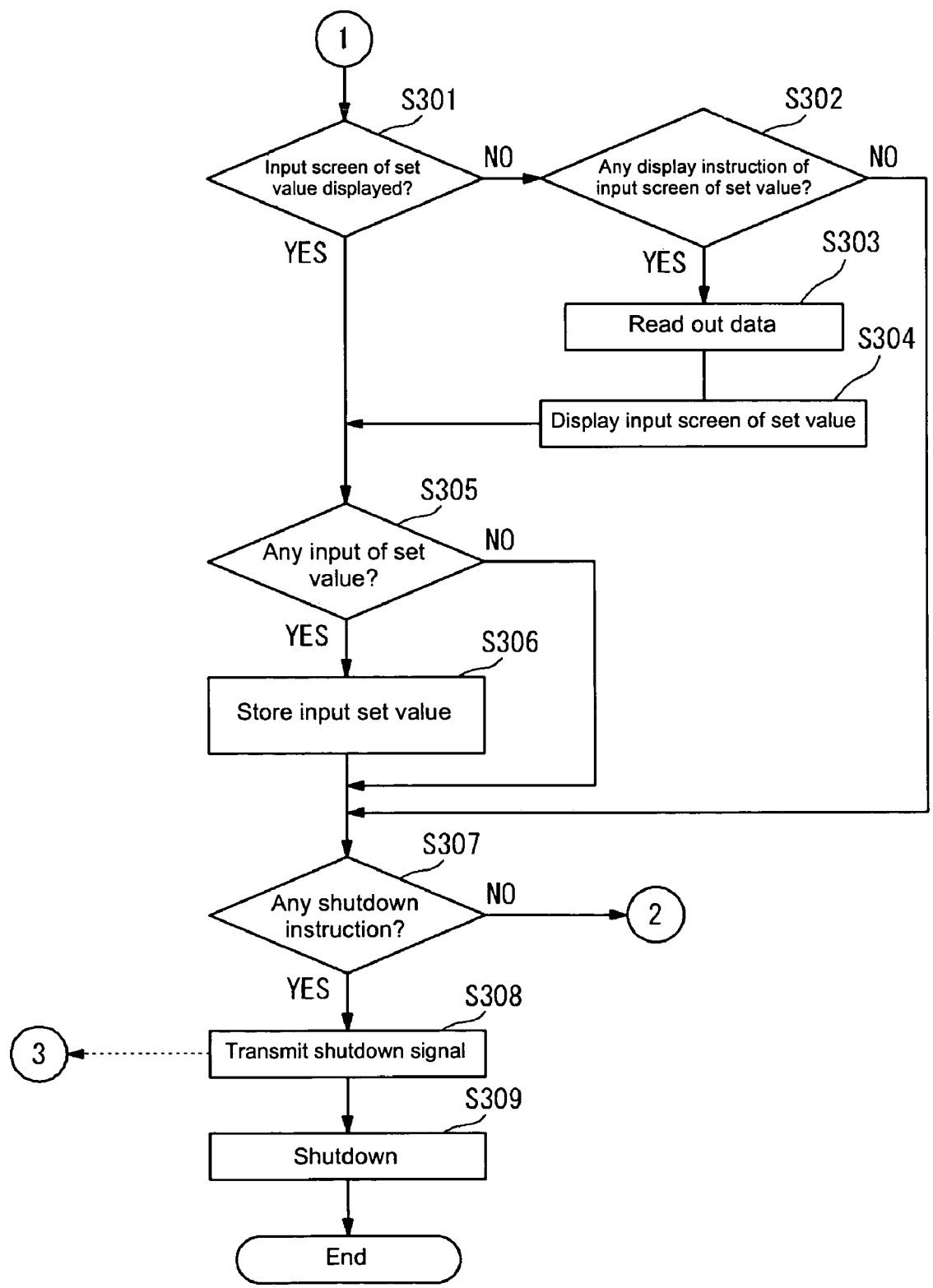
FIG. 16 is a view showing an overall flow of one example of a process by the device.

The overall flow of one example of the process by the device is shown in FIGS. 15 and 16. In the judgment in the following flowchart, down refers to Yes and right (left) refers to No unless specifically written as "Yes" and "No". The processes described below are all processes controlled by the control member 77 and the body controller 10.

When the power of the device body 20 is turned ON, initialization of the body controller 10 is performed (step S1). In this initialization operation, initialization of the program, return to an origin position for the driving member of the device body 20, and the like are performed.

When the power of the data processing unit 12 or the personal computer is turned ON, initialization of the control member 77 is performed (step S201). In this initialization operation, initialization of the program or the like is performed. After the initialization is completed, a menu screen (not shown) including an input screen display button for instructing the display of an input screen is displayed on the display member 79. The user can operate the input member 78 to select the input screen button for instructing the display of the input screen of the menu screen.

In step S202, the control member 77 of the data processing unit 12 determines whether or not the input screen is being displayed. The control member 77 advances the process to step S205 if determined that the input screen is being displayed (Yes), and advances the process to step S203 if determined that the input screen is not being displayed (No).

In step S203, the control member 77 of the data processing unit 12 determines whether or not a display instruction of the input screen has been made (that is, whether or not input screen button for instructing the display of the input screen of the menu screen is selected). The control member 77 advances the process to step S204 if determined that the display instruction of the input screen has been made (Yes), and advances the process to step S301 if determined that the display instruction of the input screen has not been made (No).

In step S204, the control member 77 of the data processing unit 12 displays the input screen on the display member 79.

In step S205, the user operates the input member 78 to input sample information such as ID number and age of the cancer patient to be examined. Thereafter, in step S206, the information input with the input member 78 are stored in the hard disc 91g. The instruction to start the measurement is made by having the user operate the input member 78 of the personal computer 12 and select a start button displayed on the input screen.

In step S207, the control member 77 determines whether or not the instruction to start the measurement is made. The control member 77 advances the process to step S208 if determined that the instruction to start the measurement is made (Yes), and advances the process to step S301 if determined that the instruction to start the measurement is not made (No). In step S208, a measurement start signal is transmitted from the control member 77 to the body controller 10.

In step S2, the body controller 10 determines whether or not the measurement start signal is received. The body controller 10 advances the process to step S3 if determined that the measurement start signal has been received (Yes), and advances the process to step S8 if determined that the measurement start signal has not been received (No).

In step S3, the process to prepare the specimen for expression level measurement is performed. The sample is aspirated from the sample container set in the first reagent setting member 5 in step S3. A predetermined process is performed on the aspirated sample, and the specimen for expression level measurement is prepared.

In step S4, the process to prepare the specimen for activity value measurement is performed. The sample is aspirated from the sample container set in the first reagent setting member 5. A predetermined process is performed on the aspirated sample, and the specimen for activity value measurement is prepared.

In step S5, the tip setting member 1 set with the solid phase tip for protein 101 including the specimen for expression level measurement and the specimen for activity value measurement is moved into the detecting member 4 from the position shown in FIG. 1.

In step S6, excitation light is irradiated on each well of the solid phase tip for protein 101, and fluorescence radiated from each specimen is detected.

In step S7, the detected detection result is transmitted from the body controller 10 to the control member 77 of the personal computer 12.

In step S209, the control member 77 determines whether or not the detection result is received. The control member 77 advances the process to step S210 if determined that the detection result has been received (Yes). The control member 77 again executes the process of step S209 if determined that the detection result has not been received (No).

In step S210, the control member 77 executes an analyzing process from the acquired detection result.

In step S211, the control member 77 outputs the specific activity of each CDK and result of recurrence rate calculated in step S210 and the created distribution diagram as result of analysis, and displays the same on the display member 79.

Figure 20:
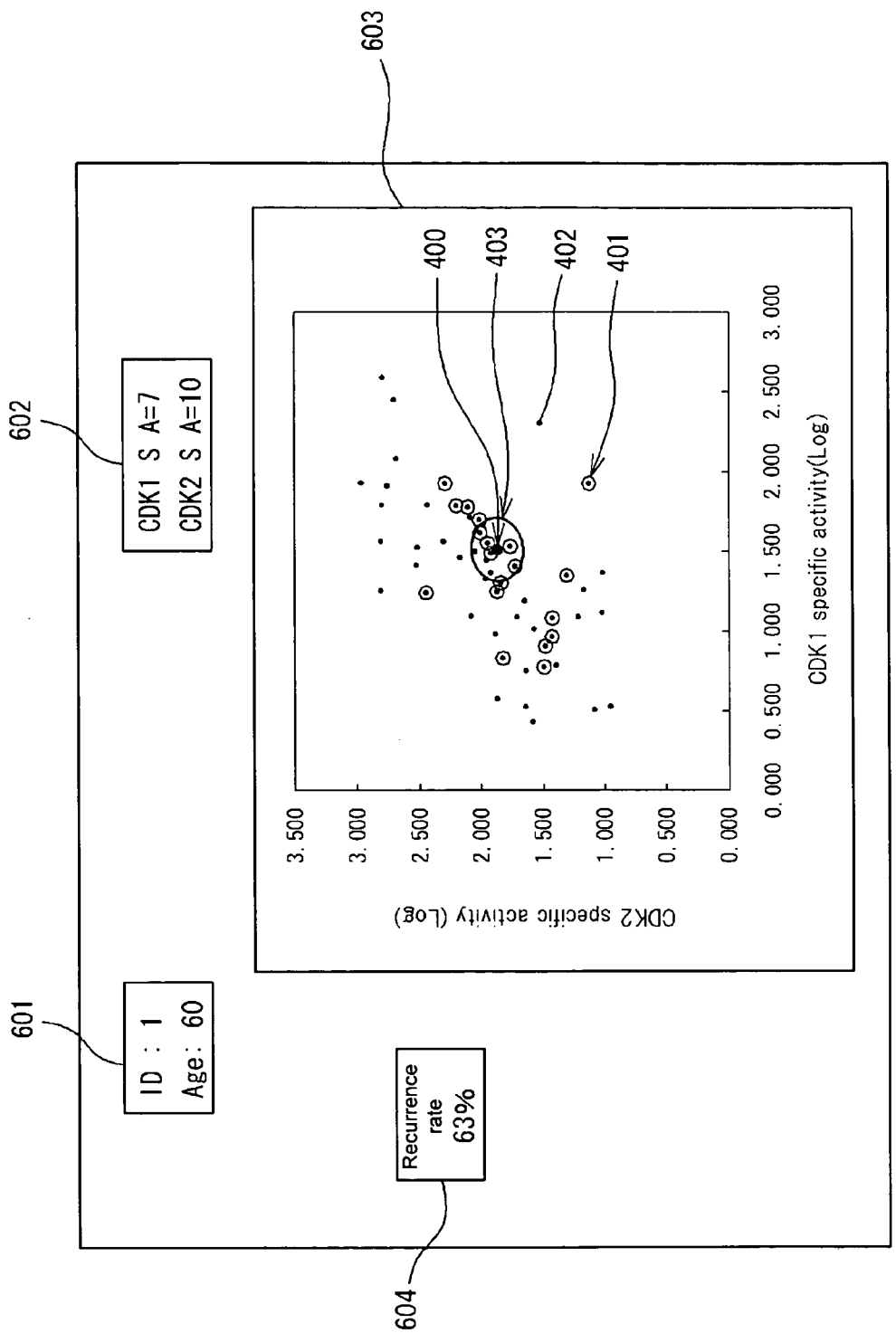
FIG. 20 is a view showing an example of a display screen.

FIG. 20 shows one example of a display screen. In the display screen shown in FIG. 20, ID number, age, and the like of the cancer patient to be examined are displayed on a display region 601 as information on the cancer patient to be examined. The CDK1 specific activity value and the CDK2 specific activity value of the malignant tumor of the cancer patient to be examined are displayed on an information display region 602 as information on the cancer patient to be examined. A graph having the CDK1 specific activity or first parameter and the CDK 2 specific activity or the second parameter of the malignant tumor of the cancer patient as two axes is displayed on a distribution diagram display region 603. The result of recurrence rate calculated in step S210 is displayed on an information display region 604 as information related to recurrence.

In step S301, the control member 77 determines whether or not an input screen of the set values of the value (radius) for determining the sample data extraction range is being displayed. The control member 77 advances the process to step S305 if determined that the input screen of the set value is being displayed (Yes), and advances the process to step S302 if determined that the input screen of the set value is not being displayed (No).

In step S302, the control member 77 determines whether or not a display instruction of the input screen of the set value has been made. The control member 77 advances the process to step S303 if determined that the display instruction of the input screen of the set value has been made (Yes), and advances the process to step S307 if determined that the display instruction of the input screen of the set value has not been made (No).

In step S303, the RAM 91g of the control member 77 reads out data of the value (radius) for determining the sample data extraction range stored in the first database 91i of the hard disc 91g.

In step S304, the input screen of the set value is displayed on the display member 79 by the control member 77. New values are input for the set values of the value for determining the sample data extraction range by having the user operate the input member 78.

In step S305, the control member 77 determines whether or not the input of the set value has been made. The control member 77 advances the process to step S306 if determined that the input of the set value has been made (Yes), and advances the process to step S307 if determined that the input of the set value has not been made (No).

In step S306, the input new set value is stored in the first database 91i of the hard disc 91g.

In step S307, the control member 77 determines whether or not an instruction to shutdown is accepted. The control member 77 advances the process to step S308 if determined that the instruction to shutdown is accepted (Yes), and returns the process to step S202 if determined that the instruction to shutdown is not accepted (No). In step S308, a shutdown signal is transmitted from the control member 77 to the body controller 10. In step S309, the control member 77 performs the process of shutting down the personal computer 12, and completes the process.

In step S8, the body controller 10 determines whether or not the shutdown signal has been received. The body controller 10 advances the process to step S9 if determined that the shutdown signal has been received (Yes), and returns the process to step S2 if determined that the shutdown signal has not been received (No). In step S9, the body controller 10 shuts down the device body 20, and terminates the process.

(4) Preparation Process of Expression Level Measurement Specimen

Figure 17:
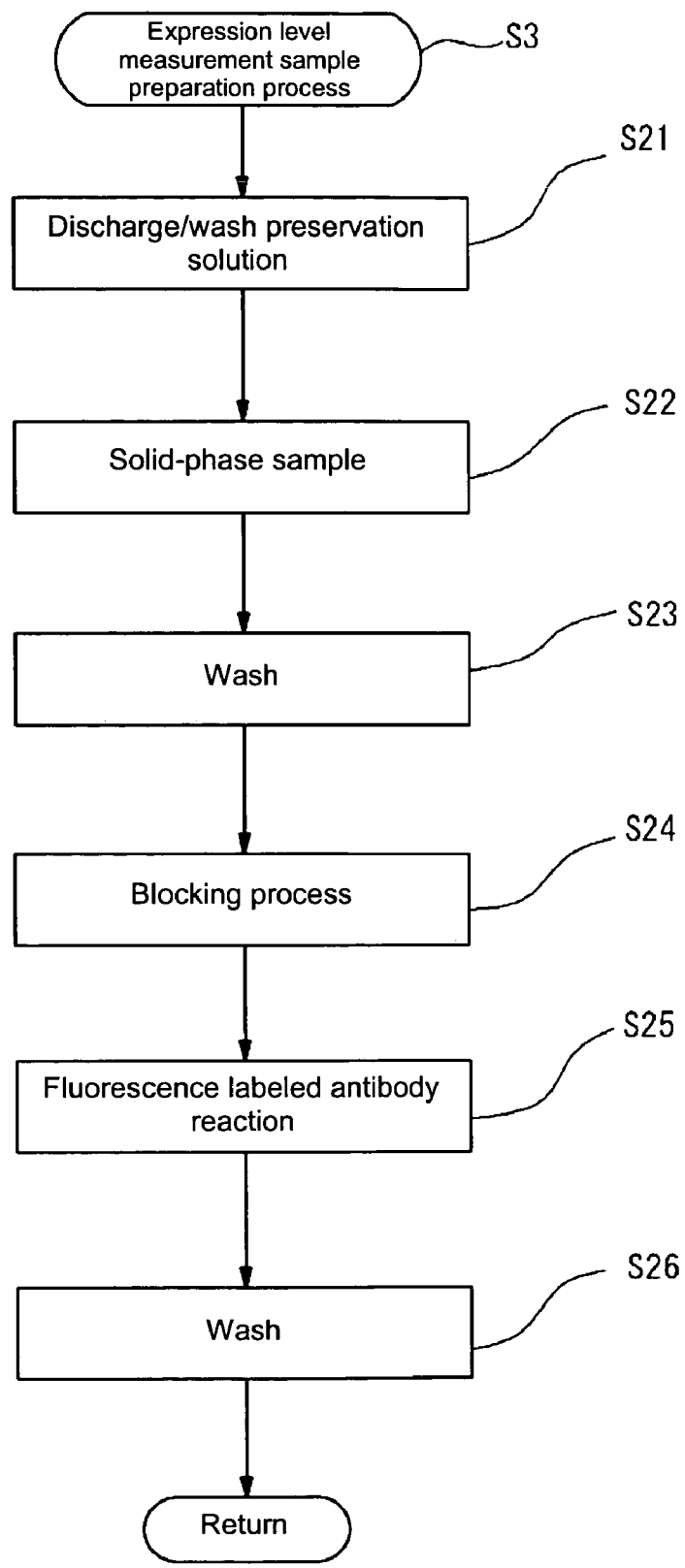
FIG. 17 is a view showing a flow of one example of a preparation process of the expression level measurement specimen.

The flow of one example of the preparation process of the expression level measurement specimen in step S3 is shown in FIG. 17.

First, in step S21, the preservation solution stored in advance in each well of the solid phase tip for protein is discharged, and the inside of each well is washed. The washing is performed by injecting washing liquid to each well from the upper side through the pipette of the dispensing mechanism member 3, and aspirating the injected washing liquid through the porous film by negative pressure from the lower side of the solid phase tip for protein. The following washing step is similarly carried out.

The sample for the expression level measurement is aspirated with the pipette from the sample container set in the first reagent setting member 5, which sample is injected to a plurality of predetermined wells, and the sample is aspirated by negative pressure from the lower side of the solid phase tip for protein. The protein is solid-phased at the porous film of the solid phase tip for protein (step S22).

Similar to step S21, the inside of the predetermined well is washed with the washing liquid. Accordingly, the components other than the protein are removed from the porous film of the solid phase tip for protein (step S23).

Subsequently, the blocking liquid is injected to the predetermined well, and after leaving it for 15 minutes or longer (e.g., for 30 minutes), the blocking liquid remaining in the well is discharged (step S24). Accordingly, the fluorescence labeled CDK1 antibody (fluorescence labeled CDK1 antibody) and the fluorescence labeled CDK2 antibody (fluorescence labeled CDK2 antibody) are prevented from being solid-phased at the site of the porous film at which the protein is not solid-phased. The commercially available fluorescence labeled CDK1 antibody and the fluorescence labeled CDK2 antibody may be used.

The fluorescence labeled CDK1 antibody and the fluorescence labeled CDK2 antibody are respectively injected to the predetermined well. In this case, each fluorescence labeled antibody is injected into two wells. The injected fluorescence label is discharged after 20 to 30 minutes have elapsed and the reaction of the fluorescence labeled antibody and the protein (CDK1 or CDK2) solid-phased on the porous film is terminated (step S25).

Lastly, similar to step S23, the inside of the predetermined well is washed with the washing liquid (Step S26).

(5) Preparation Process of Activity Value Measurement Specimen

Figure 18:
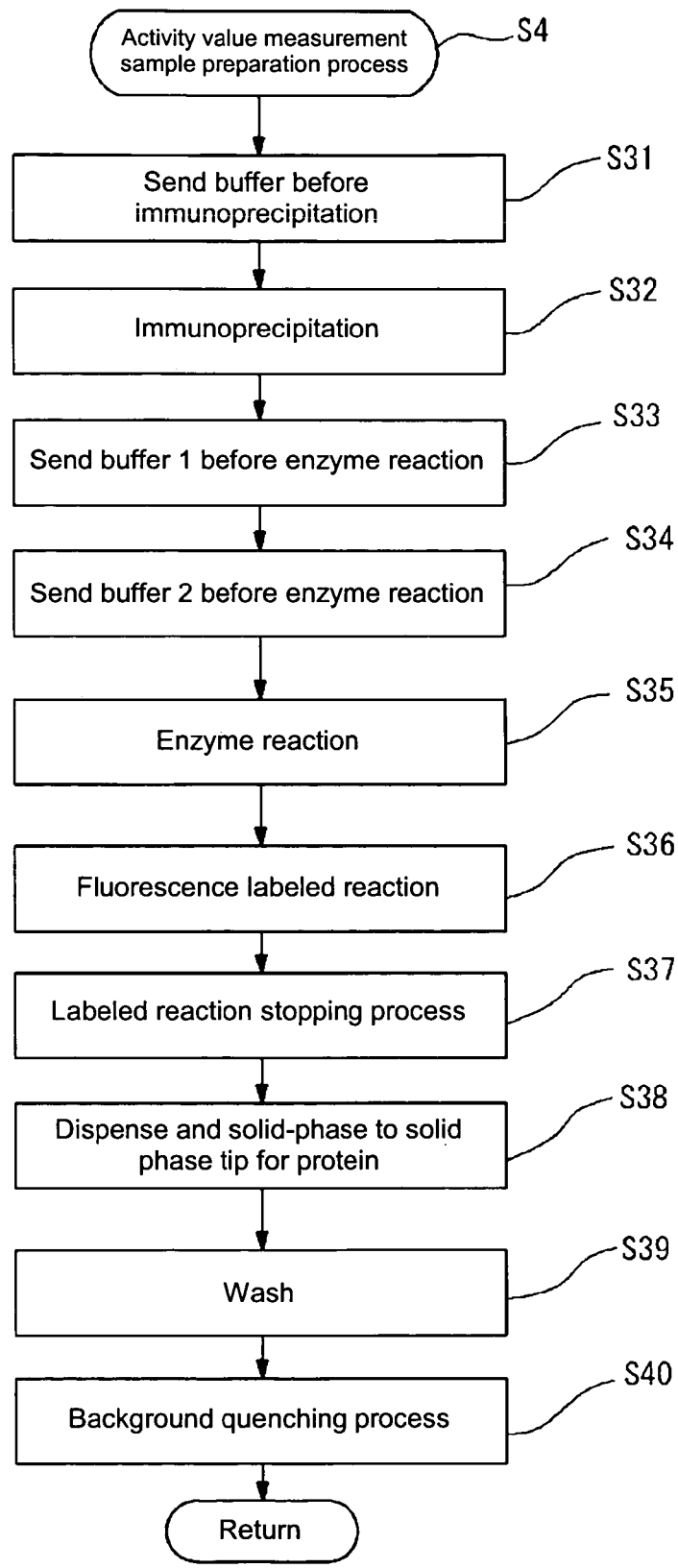
FIG. 18 is a view showing a flow of one example of a preparation process of the activity measurement specimen.

FIG. 18 shows a flow of one example of the preparation process of the activity value measurement specimen in step S4. In the preparation process of the activity value measurement specimen, four specimen preparation members 211 are arranged on the near side in the figure and four specimen preparation members 211 are arranged on the far side in the figure as the activity measurement unit 2 shown in FIG. 1. Each specimen preparation member 211 of the activity measurement unit 2 includes a first specimen preparation member (Ac1), a second specimen preparation member (Ac2), a third specimen preparation member (Ac3), and a fourth specimen preparation member (Ac4), from the left on the far side of the figure, and a fifth specimen preparation member (Ac5), a sixth specimen preparation member (Ac6), a seventh specimen preparation member (Ac7), and an eighth specimen preparation member (Ac8), from the left on the near side of the figure.

For each of the first to the eighth specimen preparation members (Ac1 to Ac8), a buffer or a washing reagent is injected to the opening 205 with the pipette of the dispensing mechanism member 3. For each of the first to the eighth specimen preparation members (Ac1 to Ac8), the syringe pump 214 and the electromagnetic valve 225 operate as described above, so that the buffer of the liquid storage member 204 passes through the carrier 206 into the flow channel 223, and again passes through the carrier 206 and returns to the liquid storage member 204. The buffer returned to the liquid storage member 204 in all the columns 201 is aspirated and discarded with the pipette of the dispensing mechanical member 3 (step S31).

Immunoprecipitation (immunoreaction between antibody and CDK) is then performed (step S32). First, the sample 1 for the activity value measurement is aspirated with one pipette and the sample 2 for the activity value measurement is aspirated with another pipette from one sample container set in the first reagent setting member 5.

Figure 26:
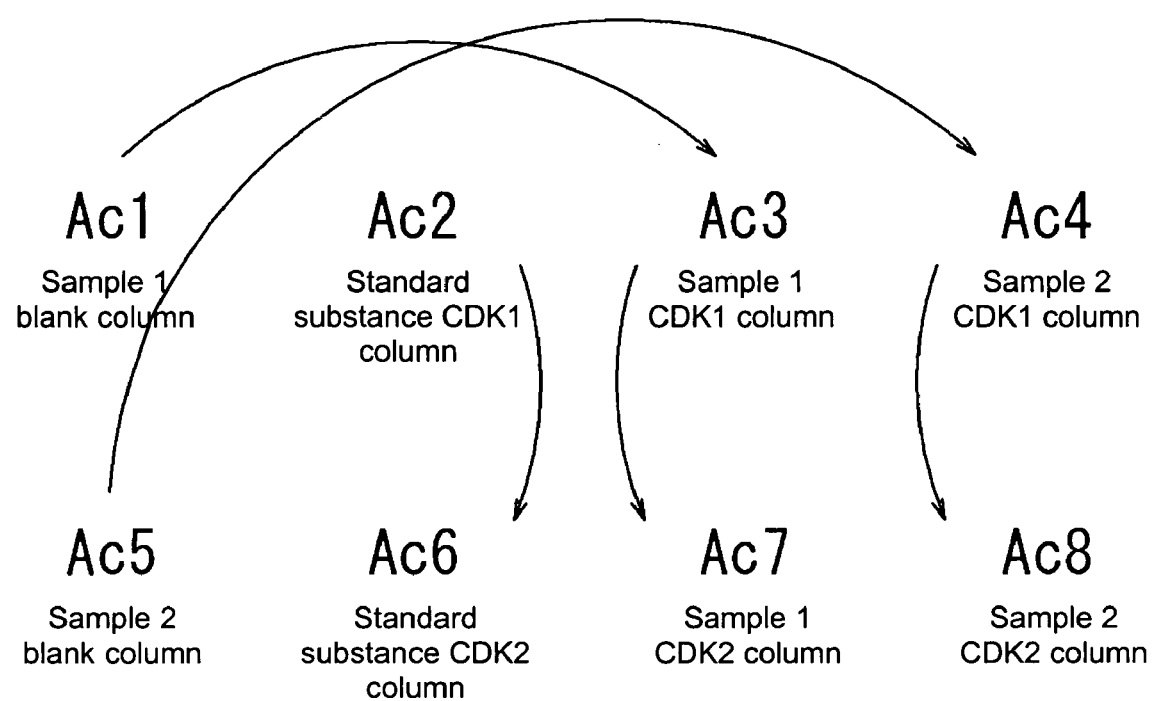
FIG. 26 is an explanatory view showing the usage procedures of the sample and the like in the device.

As shown in FIG. 26, the sample 1 for the activity value measurement aspirated from the sample container is first injected to the liquid storage member 204 of the first specimen preparation member (Ac1). The sample 1 is sent to the carrier 206 of the first specimen preparation member (Ac1) by operating the syringe pump 214 and the electromagnetic valve 225 as described above. In this case, the sample 1 reciprocates in the carrier 206 of the column 201 once by reciprocating the piston 218 up and down once (aspiration→discharge).

The sample 2 for activity value measurement aspirated from the sample container is first injected to the liquid storage member 204 of the fifth specimen preparation member (Ac5). The sample 2 is similarly sent to the carrier 206 of the fifth specimen preparation member (Ac5), similar to the above.

Neither antibody of the CDK1 nor antibody of the CDK2 is immobilized on the carrier 206 of the columns 201 of the first specimen preparation member (Ac1) and the fifth specimen preparation member (Ac5). Therefore, the CDK1 and the CDK2 are not solid-phased in the first specimen preparation member (Ac1) and the fifth specimen preparation member (Ac5), the sample 1 containing the CDK1 and the CDK2 is stored in the column 201 of the first specimen preparation member (Ac1), and the sample 2 containing the CDK1 and the CDK2 is stored in the column 201 of the fifth specimen preparation member (Ac5).

The sample 1 stored in the column 201 of the first specimen preparation member (Ac1) is then aspirated with the pipette, and injected to the liquid storage member 204 of the third specimen preparation member (Ac3). The sample 1 is then sent to the carrier 206 of the third specimen preparation member (Ac3), similar to the above.

The sample 2 stored in the column 201 of the fifth sample specimen member (Ac5) is aspirated with the pipette, and injected to the liquid storage member 204 of the fourth specimen preparation member (Ac4). The sample 2 is then sent to the carrier 206 of the fourth specimen preparation member (Ac4), similar to the above.

The antibody of the CDK1 is immobilized to the carriers 206 of the columns 201 of the third specimen preparation member (Ac3) and the fourth specimen preparation member (Ac4). Therefore, the CDK1 is solid-phased but the CDK2 is not solid-phased in the third specimen preparation member (Ac3) and the fourth specimen preparation member (Ac4), the sample 1 not containing the CDK1 but containing the CDK2 is stored in the column 201 of the third specimen preparation member (Ac3), and the sample 2 not containing the CDK1 but containing the CDK2 is stored in the column 201 of the fourth specimen preparation member (Ac4).

The sample 1 stored in the column 201 of the third specimen preparation member (Ac3) is then aspirated with the pipette, and injected to the liquid storage member 204 of the seventh specimen preparation member (Ac7). The sample 1 is then sent to the carrier 206 of the seventh specimen preparation member (Ac7), similar to the above.

The sample 2 stored in the column 201 of the fourth specimen preparation member (Ac4) is aspirated with the pipette, and injected to the liquid storage member 204 of the eighth specimen preparation member (Ac8). The sample 2 is then sent to the carrier 206 of the eighth specimen preparation member (Ac8), similar to the above.

The antibody of the CDK2 is immobilized to the carrier 206 of the columns 201 of the seventh specimen preparation member (Ac7) and the eighth specimen preparation member (Ac8). Therefore, the CDK2 is solid-phased in the seventh specimen preparation member (Ac7) and the eighth specimen preparation member (Ac8), and thus the sample 1 not containing the CDK1 nor the CDK2 is stored in the column 201 of the seventh specimen preparation member (Ac7), and the sample 2 not containing the CDK1 nor the CDK2 is stored in the column 201 of the eighth specimen preparation member (Ac8).

The sample 1 and the sample 2 stored in the columns 201 of the seventh specimen preparation member (Ac7) and the eighth specimen preparation member (Ac8) are respectively aspirated with the pipette, and disposed in the waste bath 7.

The first specimen preparation member (Ac1) and the fifth specimen preparation member (Ac5) are used for activity measurement of the background, the third specimen preparation member (Ac3) and the fourth specimen preparation member (Ac4) are used for activity measurement of the CDK1, and the seventh specimen preparation member (Ac7) and the eighth specimen preparation member (Ac8) are used for activity measurement of the CDK2.

Therefore, the background activity measurement, the CDK1 activity measurement, and the CDK2 activity measurement can be performed with small amount of sample by injecting the sample remaining in the column into other columns.

The buffer 1 is then sent to the columns 201 to wash and remove unnecessary components in the sample (step S33).

Subsequently, since the buffer 1 influences enzyme reaction executed in step S25, the buffer 2 is sent to the column 201 to wash off the components of the buffer 1 with the main aim of creating a condition for the relevant enzyme reaction (step S34).

The substrate reaction solution containing substrate Histon H1 and ATPγS is then injected to the column 201, and the piston 219 is allowed to reciprocate once (step S35). The liquid pushed out from the lower side of the column 201 is stored in the column 201 as it is. According to such step, the phosphate group is introduced to the Histon H1 with CDK1 and CDK2 as enzymes. The amount of phosphate group is influenced by the strength (i.e., activity value) of the work of the CDK1 or the CDK2 as enzyme, and thus the activity values of the CDK1 or the CDK2 can be obtained by measuring the amount of phosphate group. The background activity value obtained using the first specimen preparation member (Ac1) and the fifth specimen preparation member (Ac5) shown in FIG. 26 is used to perform background correction as hereinafter described.

The fluorescent labeled reagent is dispensed directly into the column 201 from the upper of the column 201 with the pipette to bind the fluorescent labeled substance to the phosphate group introduced into the Histon H1 (step S36). In this case, the pipette repeats aspiration and discharge of liquid in the column for a predetermined time to stir the liquid in the column 201.

A reaction stopping solution is directly dispensed to the column 201 similar to the fluorescent labeled reagent after elapse of a predetermined time (e.g., for twenty minutes) from the start of step S26. The liquid in the column 201 is stirred by repeating aspiration and discharge of the liquid in the column for a predetermined time similar to step S26 (step S37). The binding of fluorescent label is thereby stopped.

The liquid in the columns 201 of the first specimen preparation member (Ac1), the third specimen preparation member (Ac3), the fourth specimen preparation member (Ac4), the fifth specimen preparation member (Ac5), the seventh specimen preparation member (Ac7), and the eighth specimen preparation member (Ac8) are injected to six wells of the solid phase tip for protein 101, and the solid phase tip for protein 101 is aspirated from the lower side (step S38). The Histon H1 containing phosphate group bound with fluorescent labeled substance is thereby solid-phased on the porous film of the phase tip for protein 101.

The well is washed similar to step S21 in the preparation process of expression level measurement specimen (step S39).

Lastly, an operation of dispensing and discharging quenching reagent for quenching (background quenching) the fluorescent light based on the fluorescent labeled substance that did not bind to the phosphate group introduced into the Histon H1 into wells is repeated six times (step S40).

(6) Analyzing Process

Figure 19:
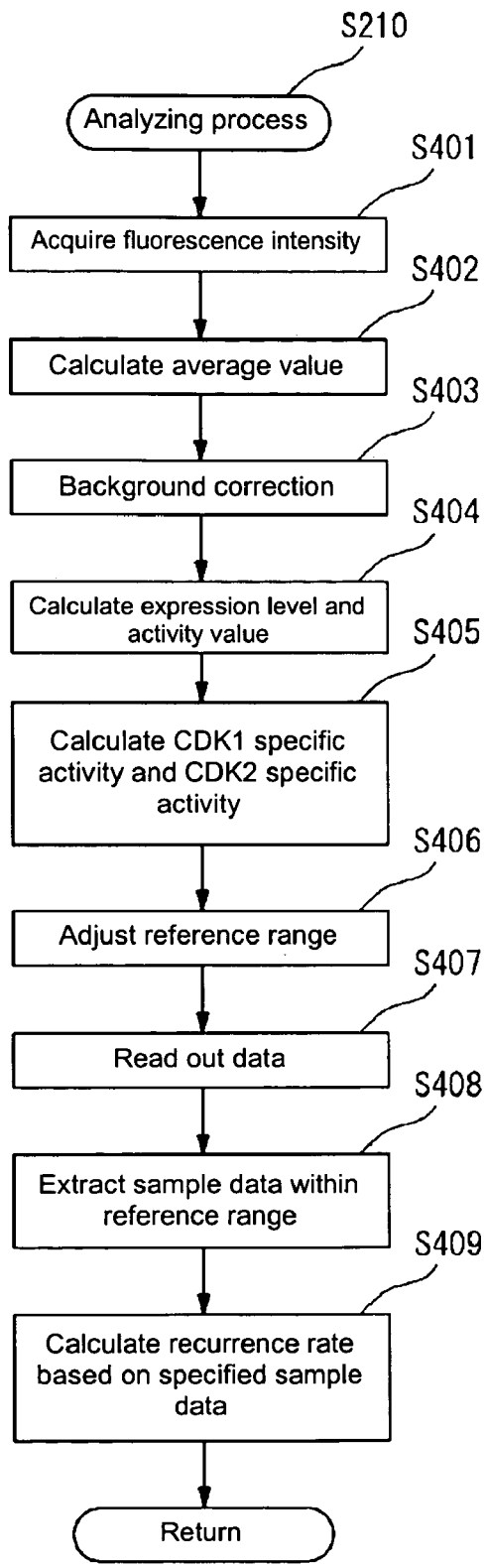
FIG. 19 is a view showing an overall flow of one example of an analyzing process by the device.

As shown in the flowchart of FIG. 19, in the step of analyzing process (step S210), analysis is performed from the fluorescence intensity obtained in the detecting member, and the result of analysis is output to the display member 79.

First, in step S401, the control member 77 acquires two fluorescence intensities for each of activity of CDK1, expression of CDK1, activity of CDK2, expression of CDK2, activity of background, and expression of background through the body controller 10 from the light receiving system of the detecting member 4.

Thereafter, the control member 77 calculates the average value of the fluorescence intensities obtained two at a time for each item in step S402.

In step S403, the background activity (average value) is subtracted from the fluorescence intensity (average value) of the CDK1 activity. The background activity (average value) is subtracted from the fluorescence intensity (average value) of the CDK2 activity. The background correction is thereby performed for the CDK1 activity and the CDK2 activity. The background correction is similarly performed for the CDK1 expression and the CDK2 expression.

In step S404, the control member 77 acquires the expression level and the activity value by using standard curve for each item. The standard curve is data for converting fluorescence intensity to expression level or activity value. The standard curve is created in advance by using two or more types of samples which expression level or activity value is known when the lot of the reagent is changed, and stored in the hard disc 91g of the control member 77.

In step S405, the control member 77 calculates the CDK1 specific activity and the CDK2 specific activity according to equation (III):

CDK1 specific activity=CDK1 activity value/CDK1 expression level

And equation (IV):

CDK2 specific activity=CDK2 activity value/CDK2 expression level

Thereafter, in step S406, the control member 77 creates a distribution diagram having a logarithm (log) of the CDK1 specific activity and a logarithm (log) of the CDK2 specific activity on two axes, and determines the sample data extraction range based on the calculated CDK1 specific activity and CDK2 specific activity. The sample data extraction range is a predetermined numerical range including the CDK1 specific activity and the CDK2 specific activity of the malignant tumor of the cancer patient to be examined. Specifically, the sample data extraction range is determined as a circle having a radius of 0.3 with a point corresponding to the logarithm (log) of the CDK1 specific activity and the logarithm (log) of the CDK2 specific activity of the malignant tumor of the cancer patient to be examined as a center in the distribution diagram having the logarithm (log) of the CDK1 specific activity and the logarithm (log) of the CDK2 specific activity on two axes. The value of radius corresponds to the numerical values of the horizontal axis and the vertical axis in the distribution diagram.

The CDK1 specific activity and the CDK2 specific activity of the malignant tumor of the cancer patient to be examined are collectively referred to as "data on cancer patient to be examined".

In step S407, the control member 77 reads out sample data in which the measurement value such as activity value and expression level of the cancer patient and the clinical information on the relevant patient are corresponded from the second database 91j of the hard disc 91g.

In step S408, the control member 77 extracts the sample data based on the sample data extraction range determined in step S406.

In step S409, the control member 77 calculates a recurrence rate based on the sample data extracted in step S408. Specifically, the recurrence rate can be calculated by counting the total number of sample data extracted in step S408 and calculating the proportion of the sample data related to the patient in whom the cancer recurred, of the sample data. The recurrence rate is shown in percentage (%) with the total number of sample data as 100.

In step S211, the control member 77 executes a process for displaying a screen as shown in FIG. 20 on the display member. The screen includes an identification information display region 601, a CDK data display region 602, a distribution diagram display region 603, and a recurrence rate display region 604.

The identification information display region 601 displays ID number and age of the cancer patient to be examined as information on the cancer patient to be examined.

The CDK data display region 602 displays the CDK1 specific activity and the CDK2 specific activity of the malignant tumor of the cancer patient to be examined as information on the cancer patient to be examined.

The recurrence rate display region 604 displays the recurrence rate calculated in step S210.

The distribution diagram display region 603 displays a graph having the CDK1 specific activity and the CDK2 specific activity as two axes. On the distribution diagram, the sample data (401, 402) of the cancer patient administered with anthracycline anticancer drugs of the sample data stored in the storage member are drawn.

The sample data 401 is plotted with sample data of the patient in whom the cancer recurred by the $1500^{th}$ day after being administered with the anthracycline anticancer drug. The sample data of the patient in whom the cancer recurred is displayed by dots surrounded by a circle as shown in FIG. 20. The sample data 402 is plotted with sample data of the patient in whom recurrence of cancer is not recognized after being administered with the anthracycline anticancer drug. The sample data of the patient in whom recurrence of cancer is not recognized is displayed only by dots as shown in FIG. 20.

The data on cancer patient to be examined 400 is plotted on the distribution diagram.

A sample data extraction range 403 determined in S406 is displayed on the distribution diagram. The distribution diagram of the display screen shown in FIG. 20 displays the CDK1 specific activity on the horizontal axis by log and the CDK2 specific activity on the vertical axis by log.

Taking the graph shown in FIG. 20 by way of example, the sample data of the cancer patient in whom the cancer recurred by the $1500^{th}$ day after being administered with the anthracycline anticancer drug tends to concentrate at a specific region of the graph (middle in the graph of FIG. 20). The data on cancer patient to be examined 400 is positioned in a region where the sample data of the patient in whom the cancer recurred concentrates. Therefore, the state of the malignant tumor of the cancer patient to be examined can be predicted to be a state similar to the malignant tumor of the cancer patient in whom the cancer recurred after being administered with the anthracycline anticancer drug. The result of calculating the recurrence rate based on the total number of sample data contained in the sample data extraction range 403 determined on the basis of the data on cancer patient to be examined 400 and the proportion of the sample data of the cancer patient in whom the recurrence of cancer is recognized is as displayed on the recurrence rate display region 604. In the example shown in FIG. 20, the recurrence rate of cancer in the cancer patient to be examined is 63%.

As shown in FIG. 20, the sample data of the patient administered with the anthracycline anticancer drug and in whom recurrence of cancer is recognized is distributed concentrating on the specific region of the two-axle graph based no the CDK1 specific activity and the CDK2 specific activity. That is, the features of the anticancer effect by the anthracycline anticancer drug are reflected on the two-axes graph of the CDK1 specific activity and the CDK2 specific activity. Thus, the sample data of the cancer patient having a specific feature in the anticancer effect by the anthracycline anticancer drug can be extracted by plotting the data cancer patient to be examined on such two-axes graph and extracting the sample data based on the plotted data on cancer patient to be examined, and thus the recurrence rate reflecting the state of the malignant tumor of the cancer patient to be examined can be obtained by calculating the recurrence rate of the cancer in the cancer patient to be examined based on the information related to the recurrence of cancer contained in the extracted sample data.

Therefore, the information on the recurrence rate provided by the device according to the first embodiment is information useful in predicting the effectiveness of the anthracycline anticancer drug in the cancer patient to be examined, and is information also useful in determining the treatment policy of the cancer patient to be examined. Therefore, the user can obtain diagnosis support information at higher precision by the diagnosis support device according to the first embodiment.

The device of the first embodiment is configured including the measurement unit 501 for measuring the activity value and the expression level of the CDK1 as well as the activity value and the expression level of the CDK2, and the solubilizing device B for obtaining a sample that can be processed in the measuring device A from a biological specimen (malignant tumor), but is not limited to such configuration. For instance, a configuration of inputting the activity values and the expression levels of the CDK1 and the CDK2 separately measured by other methods or other devices from the malignant tumor of the cancer patient to be examined through the personal computer, and performing analysis by using the input values may be adopted. Alternatively, a configuration of obtaining the CDK1 specific activity and the CDK2 specific activity in advance from the separately measured activity value and the expression level, and performing analysis by accepting the input of such values may be adopted.

The first embodiment has a configuration in which the control member 77 acquires two fluorescence intensities for each of the activity of the CDK1, the expression of the CDK1, the activity of the CDK2, the expression of the CDK2, the activity of the background, and the expression of the background, and calculates the average value of the fluorescence intensity obtained by twos for each item, but is not limited thereto, and may have a configuration in which the control member 77 acquires three or more fluorescence intensities for each of the activity of the CDK1, the expression of the CDK1, the activity of the CDK2, the expression of the CDK2, the activity of the background, and the expression of the background, and calculates the average value of the fluorescence intensity of each item.

One fluorescence intensity for each of the activity of the CDK1, the expression of the CDK1, the activity of the CDK2, the expression of the CDK2, the activity of the background, and the expression of the background may be acquired. In this case, the background correction of the activity and the expression of the CDK1 and the activity and the expression of the CDK2 is performed using the fluorescence intensity of each item acquired by one instead of the average value of each item in step S403.

In the first embodiment, the control member 77 calculates the CDK1 specific activity and the CDK2 specific activity in step S405, but the present invention is not limited thereto. For instance, in step S405, the control member 77 may calculate the inverse number of the CDK1 specific activity and the increase number of the CDK2 specific activity according to the following equation (V) in place of the CDK1 specific activity and the CDK2 specific activity:

$$\text{Inverse number of CDK1 specific activity=CDK1 expression level/CDK1 activity value}$$

and equation (VI)

$$\text{Inverse number of CDK2 specific activity=CDK2 expression level/CDK2 activity value}$$

The device of the first embodiment is configured such that the user such as doctor appropriately sets the radius of the sample data extraction range, and the sample data extraction range is determined as a circle having the set radius. The sample data extraction range is desirably determined to a size that the minimum required number of samples for ensuring the statistical reliability can be ensured. Therefore, from the standpoint of ensuring reliability, the information on the number of samples contained in the sample data extraction range may be displayed simultaneously with the display of the sample data extraction range on the display screen so that the minimum required number of samples can be ensured in the sample data extraction range. The user can then easily reset the radius of the sample data extraction range so that an appropriate number of samples can be ensured with reference to the information on the number of samples displayed on the screen.

The device of the first embodiment may automatically determine the radius of the sample data extraction range. If the device automatically sets the radius, a configuration of determining the sample data extraction range so as to satisfy the following conditions (I) to (III) is preferable.

(I) Having a range from which sample data of medically and statistically meaningful number can be extracted with the data on cancer patient to be examined as the center;

(II) Setting a region including the data on cancer patient to be examined and having a size capable of including the measurement error/standard deviation by the device;

(III) Setting a region including the data on cancer patient to be examined, and having a predetermined size including the measurement error/standard deviation of the CDK1 specific activity and the CDK2 specific activity obtained by performing one or more measurements with respect to one predetermined item for one specimen.

The diagnosis support information having medical meaning and having high precision can be provided by determining the sample data extraction range as in (I) by the control member 77. The lowering in precision caused by the measurement error by the device can be prevented by determining the sample data extraction range as in (II) by the control member 77. The lowering in precision caused by variation in the measurement values by the measurement method can be prevented by determining the sample data extraction range as in (III) by the control member 77. In step S406, the sample data extraction range is determined as above, and thus information useful in predicting the effectiveness of the anthracycline anticancer drug can be provided at high precision.

In the device of the first embodiment, the sample data extraction range is a circle having the data on cancer patient to be examined as the center, but is not limited thereto. The sample extraction range may be other shapes such as square or ellipse having the data on cancer patient to be examined as the center.

In the device of the first embodiment, the sample data extraction range is appropriately determined based on the data on cancer patient to be examined, but is not limited to such configuration. For instance, the numerical range related to the CDK1 specific activity and the CDK2 specific activity that may be the candidates of the sample data extraction range may be set in plurals in advance, and the numerical range to which the data on cancer patient to be examined belongs, of the numerical ranges, may be determined as the sample data extraction range. There may be a configuration of setting, as such numerical range, a reference value to the CDK1 specific activity and the CDK2 specific activity that can divide the cancer patients administered with the anthracycline anticancer drugs into at least two groups of different recurrence risks, and setting two ranges of the range of greater than or equal to the reference value and the range smaller than the reference value.

The reference value can be set to a statistically significant value by obtaining the CDK1 specific activity and the CDK2 specific activity of the malignant tumor of the cancer patient administered with the anthracycline anticancer drugs from a plurality of cases. Second and third embodiments using the reference value obtained in such manner are described below.

Second Embodiment

Figure 21:
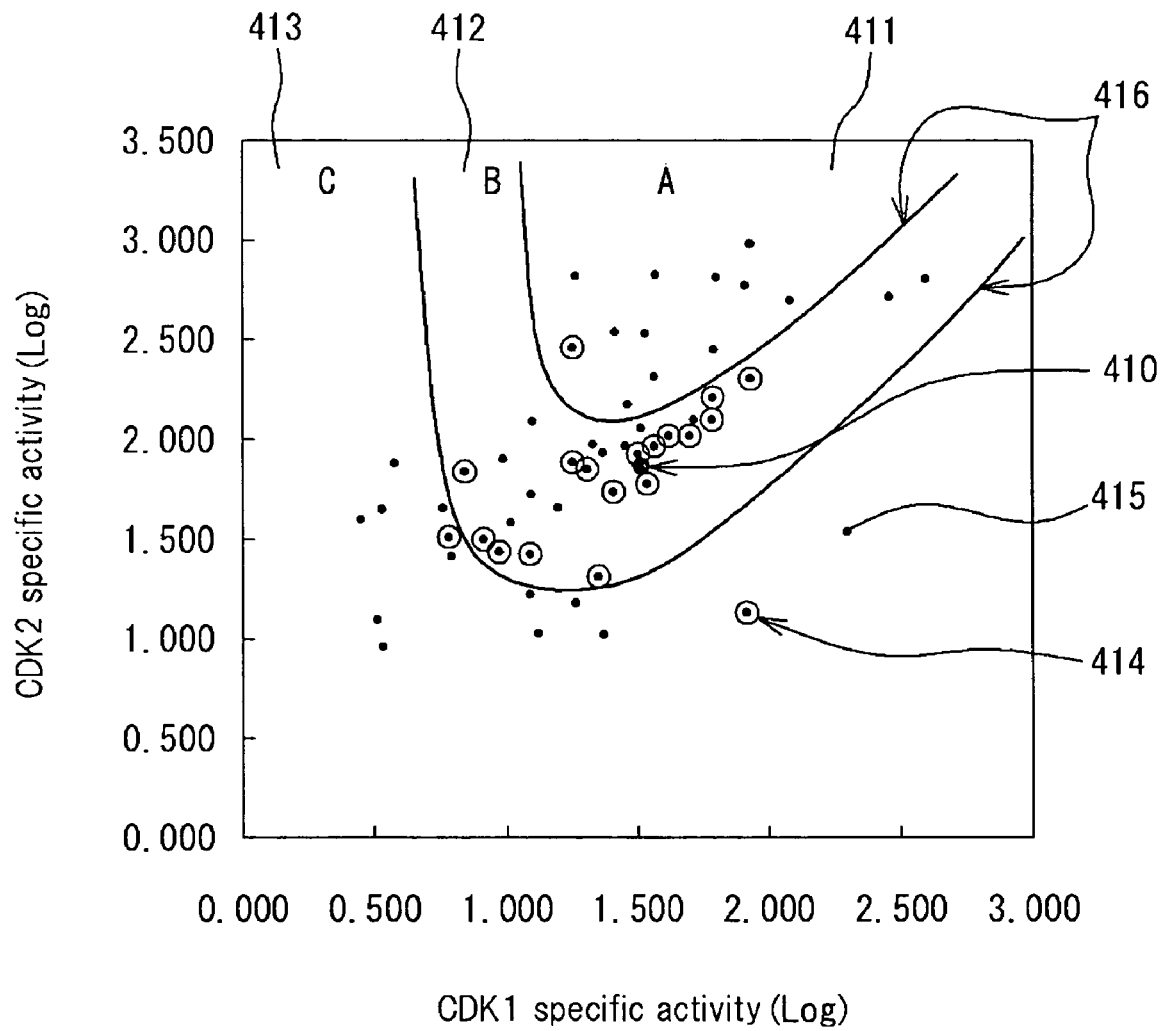
FIG. 21 is a schematic explanatory view of a graph shown on a distribution diagram display region in the display screen of a diagnosis support device of a second embodiment.

FIG. 21 is a schematic explanatory view of a graph shown in the distribution diagram display region in the display screen of the diagnosis support device of the second embodiment. In the diagnosis support device of the second embodiment, the reference value is set in advance based on the activity values and the expression levels of the CDK1 and the CDK2. In FIG. 21, a reference line 416 based on the reference value is drawn. In FIG. 21, the sample data (414, 415) of the cancer patient administered with the anthracycline anticancer drug are drawn.

The sample data 414 is plotted with the sample data of the cancer patient in whom the cancer recurred by the $1500^{th}$ day after being administered with the anthracycline anticancer drug. The sample data 415 is plotted with the sample data of the cancer patient in whom the recurrence of cancer is not recognized after being administered with the anthracycline anticancer drug. Furthermore, data on cancer patient to be examined 410 is plotted in FIG. 21.

A region 411, B region 412, and C region 413 are obtained as the sample data extraction range by the reference value (reference line) 416 of FIG. 21. The recurrence rate of the cancer in each sample data extraction range is calculated based on the presence of recurrence of the sample data contained in each sample data extraction range. This result is shown in table 2.

TABLE 2

| Region | Total number of sample data | Number of recurred sample data | Recurrence rate |
| --- | --- | --- | --- |
| A | 12 | 1 | 8% |
| B | 28 | 16 | 57% |
| C | 14 | 2 | 14% |

As shown in table 2, the recurrence rate of the A region is 8%, the recurrence rate of the B region is 57%, and the recurrence rate of the C region is 14%. In the example shown in FIG. 21, the data on cancer patient to be examined 410 is plotted in the region (B region) where the sample data of the cancer patient in whom the recurrence of cancer is recognized is concentrated. Thus, the state of the malignant tumor of the cancer patient to be examined can be assumed as a state similar to the malignant tumor of the cancer patient in whom the cancer recurred after being administered with the anthracycline anticancer drug. The data on cancer patient to be examined 410 belongs to the B region, and thus the recurrence rate of the cancer patient to be examined is calculated as 57% from table 2.

Third Embodiment

Figure 22:
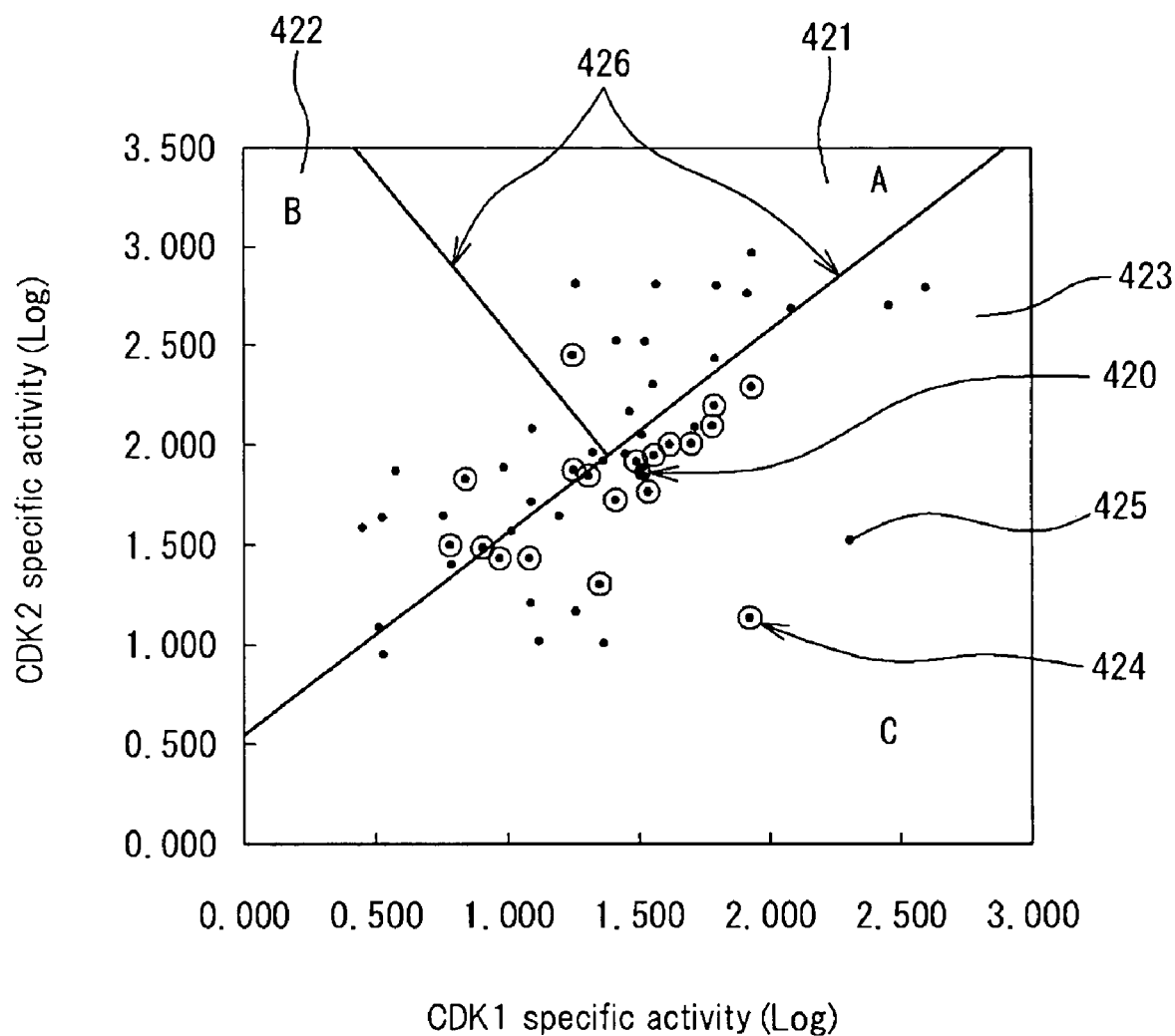
FIG. 22 is a schematic explanatory view of a graph shown on a distribution diagram display region in the display screen of a diagnosis support device of a third embodiment.

FIG. 22 is a schematic explanatory view of a graph shown in the distribution diagram display region in the display screen of the diagnosis support device of the third embodiment. In the diagnosis support device of the third embodiment, the reference value 426 is set in advance based on the information related to recurrence contained in the sample data of the cancer patient administered with the anthracycline anticancer drug. In FIG. 22, the reference value 426 (reference line) is drawn. In FIG. 22, the sample data (424, 425) of the cancer patient administered with the anthracycline anticancer drug are plotted. Specifically, the sample data 424 is plotted with the sample data of the cancer patient in whom the cancer recurred by the $1500^{th}$ day after being administered with the anthracycline anticancer drug. The sample data 425 is plotted with the sample data of the cancer patient in whom the recurrence of cancer is not recognized after being administered with the anthracycline anticancer drug. Furthermore, data on cancer patient to be examined 420 is plotted in FIG. 22.

A region 421, B region 422, and C region 423 are obtained as the sample data extraction range by the reference value (reference line) 426 of FIG. 22. The result of calculating the recurrence rate based on the presence of recurrence of cancer of the sample data contained in each sample data extraction range divided as above is shown in table 3.

TABLE 3

| Region | Total number of sample data | Number of recurred sample data | Recurrence rate |
| --- | --- | --- | --- |
| A | 12 | 1 | 8% |
| B | 14 | 3 | 21% |
| C | 28 | 14 | 50% |

As shown in table 3, the recurrence rate of the A region is 8%, the recurrence rate of the B region is 21%, and the recurrence rate of the C region is 50%. In the example shown in FIG. 22, the data on cancer patient to be examined 420 is plotted in the region (C region) where the sample data of the cancer patient in whom the cancer recurred is concentrated. Thus, the state of the malignant tumor of the cancer patient to be examined can be assumed as a state similar to the malignant tumor of the cancer patient in whom the cancer recurred after being administered with the anthracycline anticancer drug. The data cancer patient to be examined 420 belongs to the C region, and thus the recurrence rate of the cancer patient to be examined is calculated as 50% from table 3.

Figure 24:
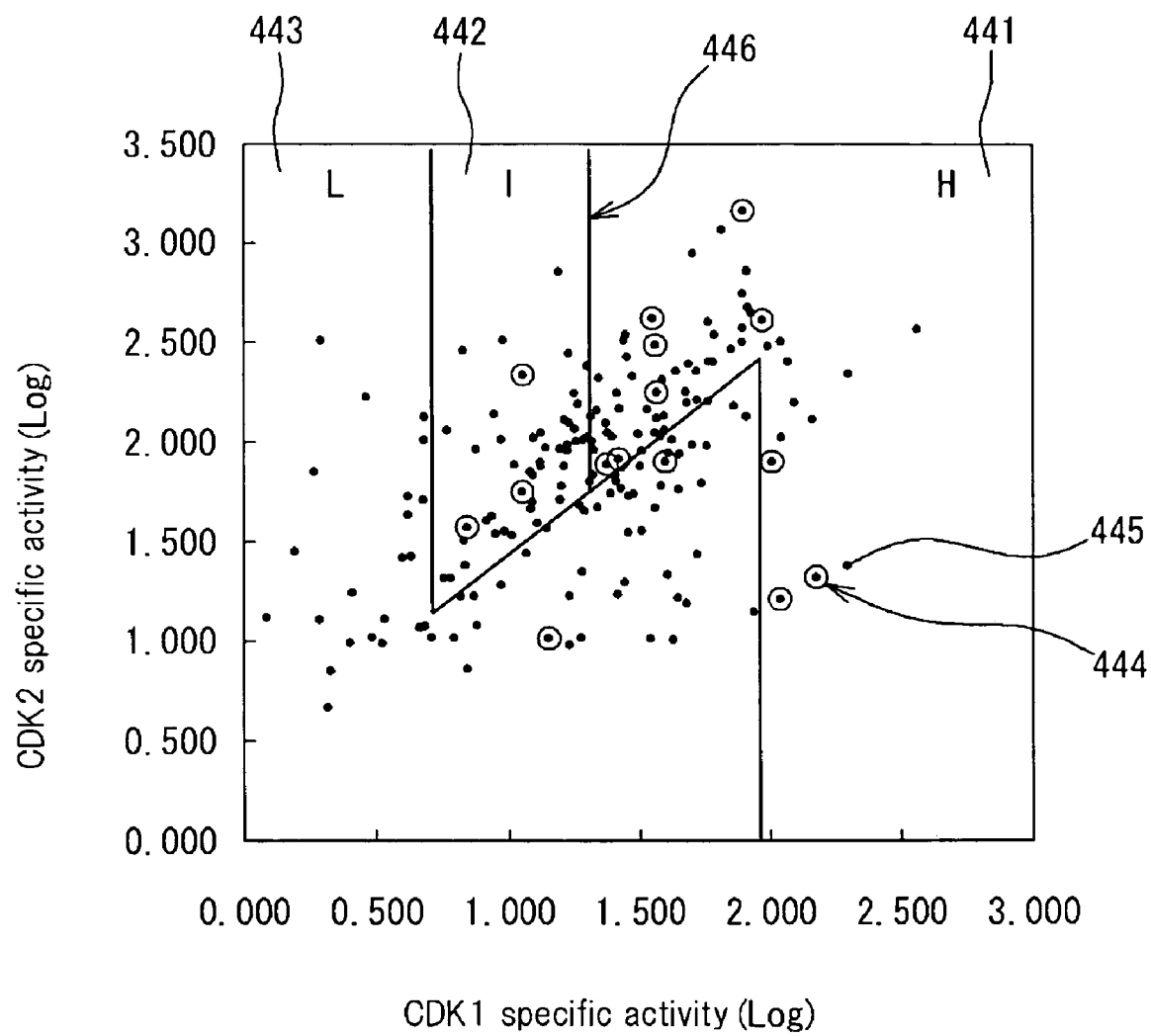
FIG. 24 is a graph showing cancer patients not treated with anticancer drug in three groups of different recurrence risks.

A reference value for classifying the cancer patient not treated with anticancer drug into groups of different recurrence risks may be set. An example using such reference value is shown in FIG. 24. FIG. 24 is a graph showing the cancer patient not treated with anticancer drug classified into three groups of different recurrence risks.

In FIG. 24, a reference value 446 capable of dividing the cancer patients treated with hormone therapy without being treated with anticancer drug into three groups of different recurrence risks is shown. The reference value 446 is calculated based on the sample data (444, 445) of the cancer patient treated with hormone therapy. Specifically, the sample data 444 is plotted with the sample data of the cancer patient in whom the cancer recurred by the $1500^{th}$ day after being treated with hormone therapy. The sample data 445 is plotted with the sample data of the cancer patient in whom the recurrence of cancer is not recognized after being treated with the hormone therapy.

The reference value 446 in FIG. 24 includes a first reference value, a second reference value, a third reference value, and a fourth reference value. Specifically, the reference values are as described below.

First reference value: ratio (specific activity ratio) of CDK1 specific activity and CDK2 specific activity is 2.8
Second reference value: specific activity of CDK1 is 5
Third reference value: specific activity of CDK1 is 20
Fourth reference value: specific activity of CDK1 is 90

The cancer patients treated with hormone therapy without being treated with anticancer drug can be divided into three groups of different recurrence risks by the reference value 446. Specifically, the cancer patients can be classified into a high risk group H (region 441) in which the recurrence rate is relatively high, a low risk group L (region 443) in which the recurrence rate is relatively low, and an intermediate risk group I (region 442) in which the recurrence rate is intermediate. The recurrence rate is calculated based on the information on the presence of recurrence of the sample data of the cancer patients treated with hormone therapy contained in the high risk group H, the intermediate risk group I, and the low risk group L of the graph of FIG. 24. The result is shown in table 4.

TABLE 4

| Risk group | Total number of sample data | Number of recurred sample data | Recurrence rate |
| --- | --- | --- | --- |
| L | 73 | 2 | 3% |
| I | 47 | 3 | 6% |
| H | 66 | 10 | 15% |

A fourth embodiment employing the reference value shown in FIG. 24 as the reference value for classifying the cancer patient administered with the anthracycline anticancer drug into groups of different recurrence risks is described below.

Fourth Embodiment

Figure 23:
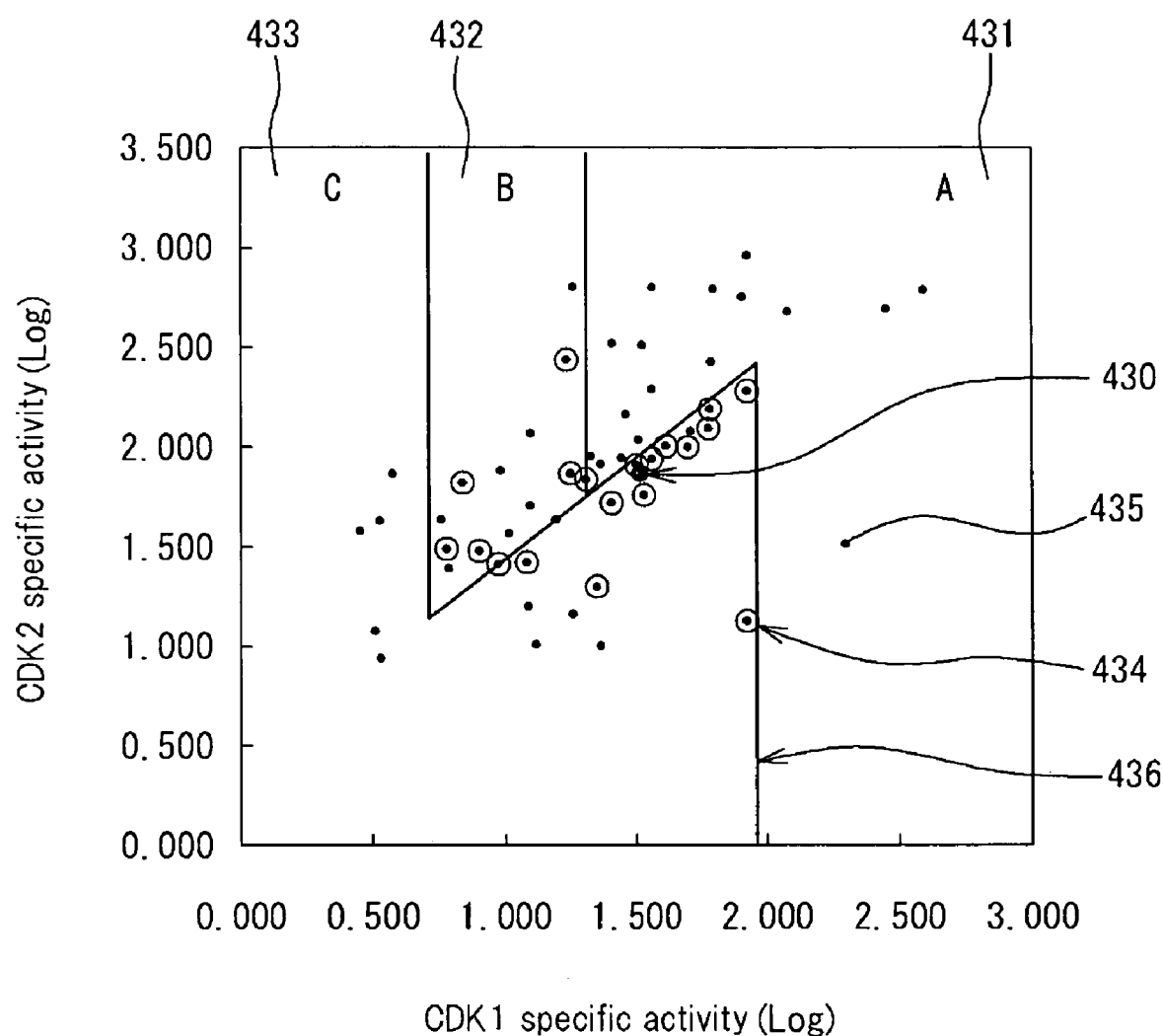
FIG. 23 is a schematic explanatory view of a graph shown on a distribution diagram display region in the display screen of a diagnosis support device of a fourth embodiment.

FIG. 23 is a schematic explanatory view of a graph shown in the distribution diagram display region in the display screen of the diagnosis support device of the fourth embodiment. In the diagnosis support device of the fourth embodiment, in the example shown in FIG. 23, a reference value 436 for classifying the cancer patient administered with anthracycline anticancer drug into groups of different recurrence risks is set in advance. The reference value 436 is drawn in FIG. 23. As described above, the reference value 436 is applied with the reference value (reference value 446 of FIG. 24) for classifying the cancer patient treated with hormone therapy without being treated with anticancer drug into groups of different recurrence risks. That is, the reference value 436 in FIG. 23 includes a first reference value, a second reference value, a third reference value, and a fourth reference value, and specifically, the reference values are as described below.

First reference value: ratio (specific activity ratio) of CDK1 specific activity and CDK2 specific activity is 2.8
Second reference value: specific activity of CDK1 is 5
Third reference value: specific activity of CDK1 is 20
Fourth reference value: specific activity of CDK1 is 90

In FIG. 23, the sample data (434, 435) of the cancer patient administered with the anthracycline anticancer drug are plotted. Specifically, the sample data 434 is plotted with the sample data of the cancer patient in whom the cancer recurred by the $1500^{th}$ day after being administered with the anthracycline anticancer drug. The sample data 435 is plotted with the sample data of the cancer patient in whom the recurrence of cancer is not recognized after being administered with the anthracycline anticancer drug. Furthermore, data cancer patient to be examined 430 is plotted in FIG. 23.

A region 431, B region 432, and C region 433 are obtained as the sample data extraction range by the reference value 436 of FIG. 23. The recurrence rate is calculated based on the information on the presence of recurrence of the sample data of the cancer patient administered with the anthracycline anticancer drug contained in each sample data extraction range divided in the above manner. This result is shown in table 5.

TABLE 5

| Region | Total number of sample data | Number of recurred sample data | Recurrence rate |
|---|---|---|---|
| A | 18 | 1 | 6% |
| B | 14 | 6 | 43% |
| C | 22 | 12 | 55% |

As shown in table 5, the recurrence rate of the A region is 6%, the recurrence rate of the B region is 43%, and the recurrence rate of the C region is 55%. From the result of FIG. 23 and table 5, it can be seen that the sample data 434 of the cancer patient in whom the cancer recurred after being administered with anthracycline anticancer drug is barely seen in the A region. The A region 431 of FIG. 23 corresponds to the high risk group H of FIG. 24. Therefore, if the data on cancer patient to be examined is contained in the A region 431, the state of the malignant tumor of the cancer patient to be examined can be predicted as a state similar to the malignant tumor of the cancer patient in whom the cancer recurred after being treated with hormone treatment without being treated with anticancer drug, and a state similar the malignant tumor of the cancer patient in whom the cancer did not recur after being administered with the anthracycline anticancer drug. The cancer patient to be examined thus can be predicted as having high recurrence risk unless administered with anticancer drug, but recurrence can be prevented by administering the anthracycline anticancer drug. In other words, it is suggested that the anthracycline anticancer drug can be predicted to be effective for the relevant cancer patient to be examined.

From the result of FIG. 23 and table 5, it can be seen that the sample data 434 of the cancer patient in whom the cancer recurred after being administered with anthracycline anticancer drug is concentrated in the B region and the C region. The B region 432 of FIG. 23 corresponds to the intermediate risk group I of FIG. 24, and the C region 433 of FIG. 23 corresponds to the low risk group L of FIG. 24. Therefore, if the data on cancer patient to be examined is contained in the B region 432 or the C region 433, the state of the malignant tumor of the cancer patient to be examined can be predicted as a state similar to the malignant tumor of the cancer patient in whom the cancer recurred after being administered with anthracycline anticancer drug. Then, it can be predicted that it is difficult to prevent recurrence even if the anthracycline anticancer drug is administered in the cancer patient to be examined. In other words, it is suggested that the anthracycline anticancer drug can be predicted to be ineffective for the relevant cancer patient to be examined.

For instance, the data on cancer patient to be examined 430 is contained in the C region 433 in FIG. 23. Thus, the state of the malignant tumor of the cancer patient to be examined can be predicted as a state similar to the malignant tumor of the cancer patient in whom the cancer recurred after being administered with anthracycline anticancer drug.

The sample data extraction range is determined as the C region 433 based on the data on cancer patient to be examined 430, and the recurrence rate of the cancer of the cancer patient to be examined is calculated based on the information on the presence of recurrence of the sample data contained in the C region 433. As a result, a value of high recurrence rate of 55% was indicated.

Therefore, the reference value corresponding to the CDK1 specific activity and the CDK2 specific activity for classifying the cancer patients not treated with anticancer drug into groups of different recurrence risks is suggested to be used as the reference value for classifying the cancer patients administered with the anthracycline anticancer drug into groups of different recurrence risks.

The recurrence rate calculated as above can be predicted as the recurrence rate reflecting the state of the malignant tumor of the cancer patient to be examined. That is, the recurrence rate calculated as above can be considered as the recurrence rate of the cancer predicted when the anthracycline anticancer drug is administered to the cancer patient to be examined. Therefore, the information on the recurrence rate provided by the device according to the fourth embodiment is information useful in predicting the effectiveness of the anthracycline anticancer drug in the cancer patient to be examined, and may be information useful in determining the treatment policy of the cancer patient to be examined.

The reference values of the second to the fourth embodiments may be appropriately set by users such as doctors.

In each of the second to the fourth embodiments, the sample data extraction range for extracting the sample data by displaying the set value input screen and inputting the set value is set, but is not limited to such configuration. The set value can be input with the following configuration.

Figure 27:
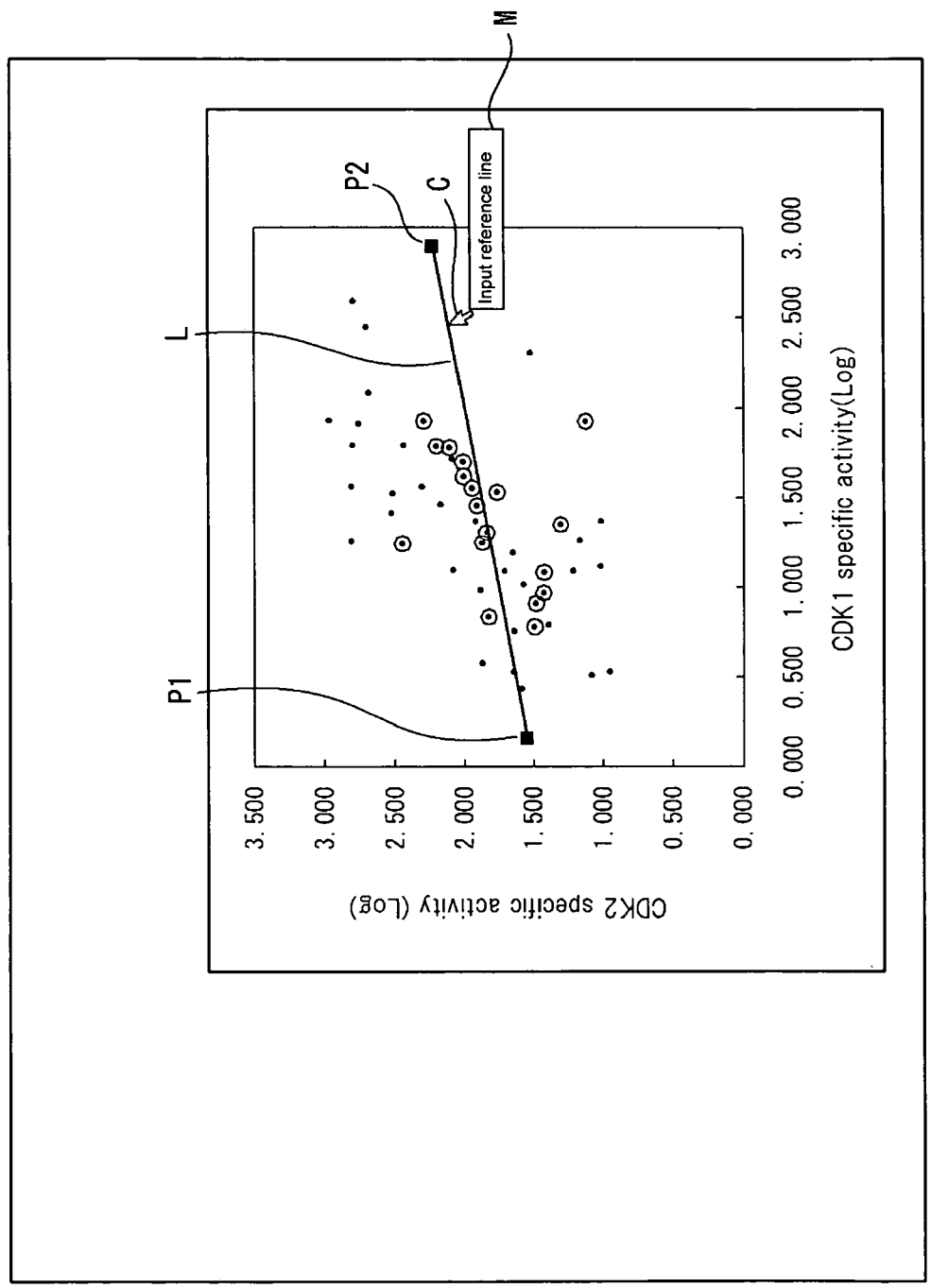
FIG. 27 is a view showing an example of the display screen.

FIG. 27 is a view showing one example of the set value input screen. First, the cursor C is moved to a predetermined position on the distribution diagram with the operation of the input member 78 (e.g., mouse) with the distribution diagram showing the sample data displayed on the set value input screen, and the mouse is double clicked to set the first set value P1. Similar operation is performed to input the second set value. The mouse is then right clicked to display a selection menu M, and the item of the displayed "reference line input" is selected to set a reference line L connecting the first set value and the second set value. The reference line as shown in FIGS. 22 and 23 can be easily set by repeating such operations.

The "reference line input" is selected after inputting three or more set values by the input member 78, so that a curve approximate to a line segment connecting each set value is set as the reference line and displayed on the distribution diagram. The reference line shown in FIG. 21 is easily set and the setting of the sample data extraction range is facilitated through such method.

[4] Prediction of Effectiveness of Anthracycline Anticancer Drug

As described in [3], the information related to the recurrence obtained by the diagnosis support device is information useful in predicting the effectiveness of the anthracycline anticancer drug. The effectiveness of the anthracycline anticancer drug thus can be predicted based on the information related to the recurrence obtained by the diagnosis support device.

In an effectiveness prediction device, a threshold value for predicting effectiveness (threshold value defined based on the recurrence rate obtained from the patients after being administered with anthracycline anticancer drug) may be stored in advance as a set value. Such effectiveness prediction device merely needs to be configured to calculate the recurrence rate, similar to the diagnosis support device of the first embodiment. The effectiveness prediction device also merely needs to be configured to predict the effectiveness of the anthracycline anticancer drug in the cancer patient to be examined by comparing the calculated recurrence rate and the threshold value. Specifically, the value of the recurrence rate and the threshold value are compared, and determination is made as "low effectiveness" if the value of the recurrence rate is greater than or equal to the threshold value, and determination is made as "high effectiveness" if the value of the recurrence rate is smaller than the threshold value.

Figure 25:
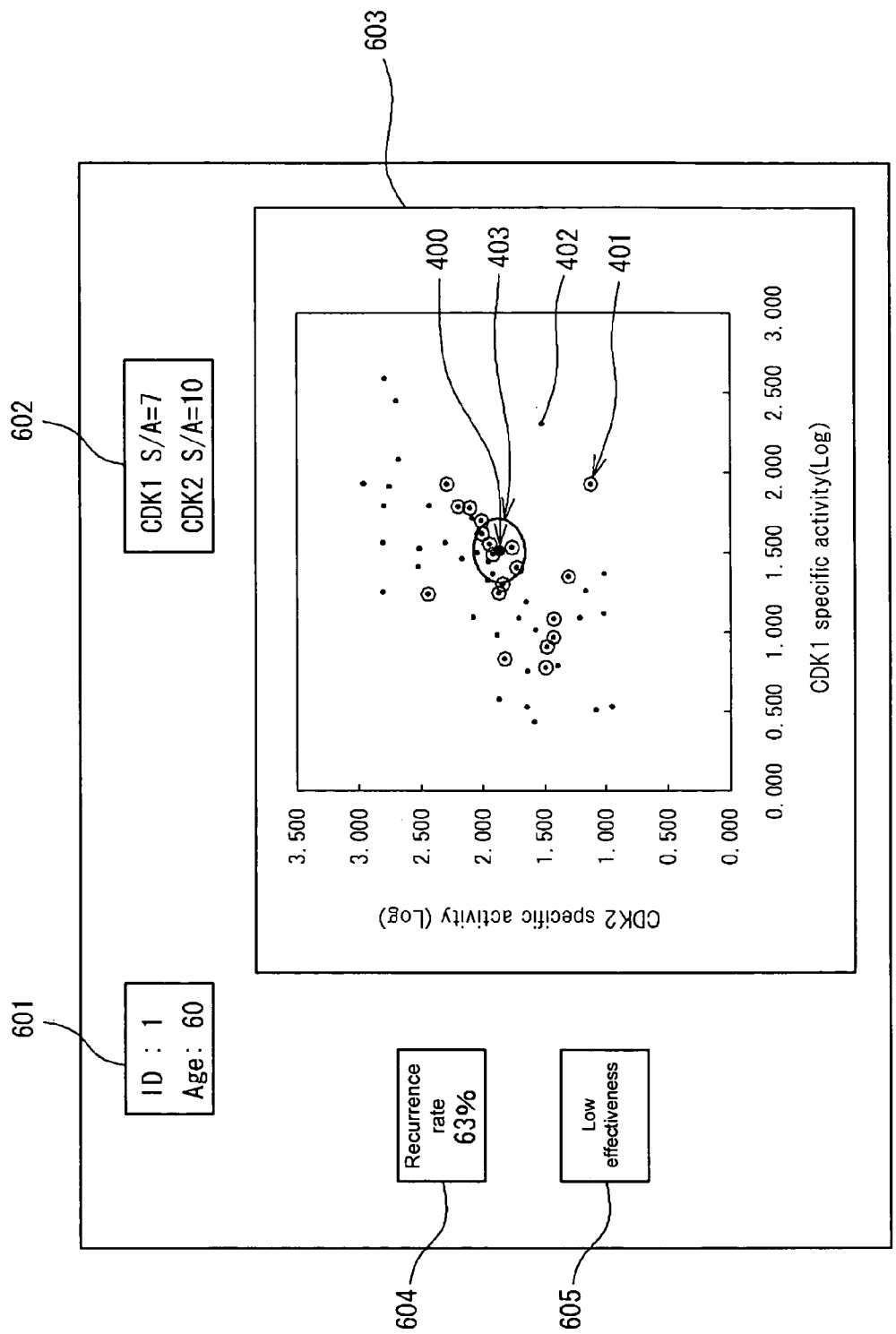
FIG. 25 is a view showing an example of the display screen.

The effectiveness prediction device is configured to display the prediction result of effectiveness as result of analysis on the display screen for outputting (displaying) the result of analysis. An example of such display screen is shown in FIG. 25. In the display screen shown in FIG. 25, ID number, age, and the like of the cancer patient to be examined are displayed on the display region 601. The information display region 602 also displays data on cancer patient to be examined, that is, the CDK1 specific activity and the CDK2 specific activity obtained from the malignant tumor of the cancer patient to be examined. A graph having the CDK1 specific activity and the CDK2 specific activity as two axes is displayed in the distribution diagram display region 603. The result of the calculated recurrence rate is displayed on the information display region 604. The determination result of effectiveness is displayed as information related to the effectiveness of the anthracycline anticancer drug in the cancer patient to be examined on the information display region 605.

With regards to other configurations and processes, the configurations and processes similar to the diagnosis support device of the first embodiment can be applied to the effectiveness prediction device.

In the effectiveness prediction device, the effectiveness is predicted (determined) based on the calculated recurrence rate, but is not limited thereto. In the second to the fourth embodiments, the sample data extraction range is determined by comparing the CDK1 specific activity and the CDK2 specific activity of the data on cancer patient to be examined with the reference value set in advance. The reference value is the reference value capable of dividing the cancer patients administered with the anthracycline anticancer drug into at least two groups of different recurrence risks, and thus the effectiveness of the anthracycline anticancer drug in the cancer patient to be examined can be predicted by determining to which group divided by the reference value the data on cancer patient to be examined belongs.

What is claimed is:

1. A cancer diagnostic device for supporting a diagnosis of a cancer comprising:
    acquiring means for acquiring a first cyclin dependent kinase (first CDK) parameter which is capable to be acquired from an activity value and an expression level of the first CDK, and a second cyclin dependent kinase (second CDK) parameter which is capable to be acquired from an activity value and an expression level of the second CDK, based on an activity value and an expression level of the first CDK contained in a first malignant tumor of a cancer patient to be examined and on an activity value and an expression level of the second CDK contained in the first malignant tumor;
    a memory storing a plurality of sample data, each of the sample data comprising:
        a first CDK parameter acquired from an activity value and an expression level of the first CDK contained in a second malignant tumor of a sample patient, to whom anthracycline anticancer drugs have been administered;
        a second CDK parameter acquired from an activity value and an expression level of the second CDK contained in the second malignant tumor; and
        information regarding a cancer recurrence of the sample patient;
    selecting means for selecting one of the sample data stored in the memory whose first CDK parameter and second CDK parameter are in a prescribed range, wherein the range contains the first CDK parameter and the second CDK parameter of the cancer patient to be examined; and
    display means for displaying the information regarding a cancer recurrence comprised in the selected sample data.

2. The device of claim 1 further comprising range setting means for setting the range.

3. The device of claim 2 wherein, the displaying means display a picture indicating a relation of the first CDK parameter and the second CDK parameter of the cancer patient to be examined with the first CDK parameter and the second CDK parameter of the sample patient, and
    the picture comprises the range set by the range setting means.

4. The device of claim 3 wherein, the picture comprises a graph indicating a relation of the first CDK parameter and the second CDK parameter of the cancer patient to be examined with the first CDK parameter and the second CDK parameter of the sample patient, and
    the graph comprises the range set by the range setting means.

5. The device of claim 4 wherein, the graph comprises an axis of first CDK parameter and an axis of second CDK parameter.

6. The device of claim 1 further comprising recurrence probability acquiring means for acquiring a probability of cancer recurrence of the cancer patient to be examined based on the information comprised in the selected sample data, wherein
    the displaying means display the probability of cancer recurrence of the cancer patient to be examined, together with the information.

7. The device of claim 1 further comprising measuring means for measuring the first malignant tumor to acquire an activity value of the first CDK, an expression level of the first CDK, an activity value of the second CDK, and an expression level of the second CDK.

8. The device of claim 1 wherein, first CDK parameter is a ratio of an activity value and an expression level of the first CDK, and
    second CDK parameter is a ratio of an activity value and an expression level of the second CDK.

9. The device of claim 1 wherein,
    information regarding a cancer recurrence indicates whether or not a cancer has recurred in a prescribed period since from the second malignant tumor had been extirpated from the sample patient.

10. A device for supporting a diagnosis of a cancer comprising:
    display; and
    controller, including a memory under control of a processor, the memory storing
    a plurality of sample data, each of the sample data comprising:

first cyclin dependent kinase (first CDK) parameter which is capable to be acquired from an activity value and an expression level of the first CDK contained in a first malignant tumor of a sample patient who has been administered anthracycline anticancer drugs;

second cyclin dependent kinase (second CDK) parameter which is capable to be acquired from an activity value and an expression level of the second CDK contained in the first malignant tumor; and information regarding a cancer recurrence of the sample patient, and instructions enabling the processor to carry out operations, comprising:

acquiring a first CDK parameter based on an activity value and an expression level of the first CDK contained in a second malignant tumor of a cancer patient to be examined, and a second CDK parameter based on an activity value and an expression level of the second CDK contained in the second malignant tumor;

selecting one of the sample data stored in the memory whose first CDK parameter and second CDK parameter are in a prescribed range, wherein the range contains the first CDK parameter and the second CDK parameter of the cancer patient to be examined; and controlling the display to display the information regarding a recurrence comprised in the selected sample data.

11. A cancer diagnostic device for predicting an effect of anthracycline anticancer drugs comprising:

acquiring means for acquiring a first cyclin dependent kinase (first CDK) parameter which is capable to be acquired from an activity value and an expression level of the first CDK, and a second cyclin dependent kinase (second CDK) parameter which is capable to be acquired from an activity value and an expression level of the second CDK, based on an activity value and an expression level of the first CDK contained in a first malignant tumor of a cancer patient to be examined and on an activity value and an expression level of the second CDK contained in the first malignant tumor;

a memory storing a plurality of sample data, each of the sample data comprising:

a first CDK parameter acquired from an activity value and an expression level of the first CDK contained in a second malignant tumor of a sample patient, who has been administered anthracycline anticancer drugs;

a second CDK parameter acquired from an activity value and an expression level of the second CDK contained in the second malignant tumor; and information regarding a cancer recurrence of the sample patient;

selecting means for selecting one of the sample data stored in the memory whose first CDK parameter and second CDK parameter are in a prescribed range, wherein the range contains the first CDK parameter and the second CDK parameter of the cancer patient to be examined;

predicting means for predicting an effects of anthracycline anticancer drugs with the cancer patient to be examined based on the information of the selected sample data; and displaying means for displaying the result of the prediction.

12. The device of claim 11 further comprising range setting means for setting the range.

13. The device of claim 12 wherein, the displaying means display a picture indicating a relation of the first CDK parameter and the second CDK parameter of the cancer patient to be examined with the first CDK parameter and the second CDK parameter of the sample patient, and the picture comprises the range set by the range setting means.

14. The device of claim 13 wherein, the picture comprises a graph indicating a relation of the first CDK parameter and the second CDK parameter of the cancer patient to be examined with the first CDK parameter and the second CDK parameter of the sample patient, and the graph comprises the range set by the range setting means.

15. The device of claim 14 wherein, the graph comprises an axis of first CDK parameter and an axis of second CDK parameter.

16. The device of claim 11 further comprising measuring means for measuring the first malignant tumor to acquire an activity value of the first CDK, an expression level of the first CDK, an activity value of the second CDK, and an expression level of the second CDK.

17. A cancer diagnostic device for predicting an effects of anthracycline anticancer drugs comprising:

acquiring means for acquiring a first cyclin dependent kinase (first CDK) parameter which is capable to be acquired from an activity value and an expression level of the first CDK, and a second cyclin dependent kinase (second CDK) parameter which is capable to be acquired from an activity value and an expression level of the second CDK, based on an activity value and an expression level of the first CDK contained in a first malignant tumor of a cancer patient to be examined and on an activity value and an expression level of the second CDK contained in the first malignant tumor;

a memory storing a standard value capable to divide a group of cancer patients into two groups different in a risk of cancer recurrence based on a first CDK parameter and a second CDK parameter, wherein the patients have not been administered anthracycline anticancer drugs;

comparing means for comparing the first CDK parameter and the second CDK parameter of the cancer patient to be examined with the standard value stored in the memory;

predicting means for predicting an effects of anthracycline anticancer drugs with the cancer patient to be examined based on the result of the comparing; and displaying means for displaying the result of prediction.

18. The device of claim 17 wherein, the displaying means display a picture indicating a relation of the first CDK parameter and the second CDK parameter of the cancer patient to be examined with the standard value.

19. The device of claim 17 further comprising setting means for setting the standard value.

20. The device of claim 17 wherein, the patients comprise a patient who has been treated with endocrine gland.

* * * * *

UNITED STATES PATENT AND TRADEMARK OFFICE
CERTIFICATE OF CORRECTION

PATENT NO. : 8,131,520 B2  
APPLICATION NO. : 12/286699  
DATED : March 6, 2012  
INVENTOR(S) : Hideki Ishihara et al.

Page 1 of 1

It is certified that error appears in the above-identified patent and that said Letters Patent is hereby corrected as shown below:

In the Claims

In column 35, claim 11, line 57, after "for predicting an" replace "effects" with --effect--.

In column 36, claim 17, line 26, after "for predicting an" replace "effects" with --effect--.

In column 36, claim 17, line 48, after "for predicting an" replace "effects" with --effect--.

Signed and Sealed this  
Nineteenth Day of June, 2012

David J. Kappos  
*Director of the United States Patent and Trademark Office*